(12) United States Patent
Walsh et al.

(10) Patent No.: US 9,149,182 B2
(45) Date of Patent: Oct. 6, 2015

(54) OPTICAL COHERENCE TOMOGRAPHY DEVICE, METHOD, AND SYSTEM

(71) Applicant: Doheny Eye Institute, Los Angeles, CA (US)

(72) Inventors: Alexander C. Walsh, Los Angeles, CA (US); Paul G. Updike, Santa Barbara, CA (US); Srinivas R. Sadda, Pasadena, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 13/717,508

(22) Filed: Dec. 17, 2012

(65) Prior Publication Data

US 2013/0201449 A1 Aug. 8, 2013

Related U.S. Application Data

(63) Continuation of application No. 12/111,894, filed on Apr. 29, 2008, now Pat. No. 8,348,429.

(60) Provisional application No. 61/040,084, filed on Mar. 27, 2008.

(51) Int. Cl.
*A61B 3/14* (2006.01)
*A61B 3/10* (2006.01)
(Continued)

(52) U.S. Cl.
CPC ............... *A61B 3/102* (2013.01); *A61B 3/0008* (2013.01); *A61B 3/0025* (2013.01); *A61B 3/0033* (2013.01); *A61B 5/7275* (2013.01); *A61B 3/1005* (2013.01); *A61B 3/111* (2013.01)
USPC .......................................... 351/210; 351/206

(58) Field of Classification Search
CPC ..... G01B 9/02091; A61B 3/102; A61B 5/0066
USPC ................... 351/204–247; 356/450, 477, 479; 600/407, 425; 382/131
See application file for complete search history.

(56) References Cited

U.S. PATENT DOCUMENTS

| 4,154,114 A | 5/1979 | Katz et al. |
| 4,237,901 A | 12/1980 | Taenzer |

(Continued)

FOREIGN PATENT DOCUMENTS

| CA | 2595324 | 7/2006 |
| CA | 2678506 | 8/2008 |

(Continued)

OTHER PUBLICATIONS

Third Office Action in Chinese Application No. 200980119252.3, dated Apr. 15, 2014 in 5 pages.

(Continued)

*Primary Examiner* — Mahidere Sahle
(74) *Attorney, Agent, or Firm* — Konobbe Martens Olson & Bear LLP

(57) ABSTRACT

In accordance with one aspect of the present invention, an optical coherence tomography instrument comprises an eyepiece for receiving at least one eye of a user is provided; a light source that outputs light that is directed through the eyepiece into the user's eye; an interferometer configured to produce optical interference using light reflected from the user's eye; an optical detector disposed so as to detect said optical interference; and electronics coupled to the detector. The electronics can be configured to perform a risk assessment analysis based on optical coherence tomography measurements obtained using the interferometer. An output device can be electrically coupled to the electronics, and may be configured to output the risk assessment to the user through the output device. The optical coherence tomography instrument can be self-administered, and the eyepiece can be a monocular system or a binocular system.

24 Claims, 18 Drawing Sheets

(51) Int. Cl.
*A61B 5/00* (2006.01)
*A61B 3/00* (2006.01)
*A61B 3/11* (2006.01)

(56) References Cited

U.S. PATENT DOCUMENTS

| | | | |
|---|---|---|---|
| 4,393,366 A | 7/1983 | Hill | |
| 4,479,931 A | 10/1984 | Lambrecht et al. | |
| 4,764,006 A | 8/1988 | Hamano et al. | |
| 4,848,340 A | 7/1989 | Bille et al. | |
| 4,930,512 A | 6/1990 | Henriksen et al. | |
| 5,005,966 A | 4/1991 | Handler et al. | |
| 5,056,522 A | 10/1991 | Matsumura et al. | |
| 5,141,302 A | 8/1992 | Arai et al. | |
| 5,214,455 A | 5/1993 | Penney et al. | |
| 5,369,454 A | 11/1994 | Reinstein et al. | |
| 5,442,412 A | 8/1995 | Frey et al. | |
| 5,491,524 A | 2/1996 | Hellmuth et al. | |
| 5,493,109 A | 2/1996 | Wei et al. | |
| 5,543,866 A | 8/1996 | Van de Velde | |
| 5,557,350 A | 9/1996 | Yano | |
| 5,776,068 A | 7/1998 | Silverman et al. | |
| 5,914,772 A | 6/1999 | Dyer | |
| 6,086,205 A | 7/2000 | Svetliza | |
| 6,112,114 A | 8/2000 | Dreher | |
| 6,293,674 B1* | 9/2001 | Huang et al. | 351/221 |
| 6,367,932 B1 | 4/2002 | Donaldson | |
| 6,439,720 B1 | 8/2002 | Graves et al. | |
| 6,450,643 B1 | 9/2002 | Wilson | |
| 6,592,223 B1 | 7/2003 | Stern et al. | |
| 6,609,794 B2 | 8/2003 | Levine | |
| 6,619,799 B1 | 9/2003 | Blum et al. | |
| 6,656,131 B2 | 12/2003 | Alster et al. | |
| 6,687,389 B2 | 2/2004 | McCartney et al. | |
| 6,692,436 B1 | 2/2004 | Bluth et al. | |
| 6,705,726 B2 | 3/2004 | Tanassi et al. | |
| 6,820,979 B1 | 11/2004 | Stark et al. | |
| 6,939,298 B2 | 9/2005 | Brown et al. | |
| 7,008,116 B2 | 3/2006 | Kobayashi et al. | |
| 7,219,996 B2 | 5/2007 | Ichikawa | |
| 7,233,312 B2 | 6/2007 | Stern et al. | |
| 7,237,898 B1 | 7/2007 | Hohla et al. | |
| 7,350,921 B2 | 4/2008 | Ridings | |
| 7,370,966 B2 | 5/2008 | Fukuma et al. | |
| 7,384,146 B2* | 6/2008 | Covannon et al. | 351/223 |
| 7,445,335 B2 | 11/2008 | Su et al. | |
| 7,458,685 B2 | 12/2008 | Liang et al. | |
| 7,549,752 B2 | 6/2009 | Peyman et al. | |
| 7,614,747 B2 | 11/2009 | Foster | |
| 7,618,372 B2 | 11/2009 | dela Houssaye | |
| 7,744,221 B2 | 6/2010 | Wei et al. | |
| 7,815,310 B2 | 10/2010 | Su et al. | |
| 7,982,881 B2 | 7/2011 | Fercher et al. | |
| 7,997,728 B2 | 8/2011 | Huang et al. | |
| 8,002,410 B2 | 8/2011 | Shea | |
| 8,079,711 B2 | 12/2011 | Stetson et al. | |
| 8,100,530 B2 | 1/2012 | Zhou et al. | |
| 8,348,429 B2 | 1/2013 | Walsh et al. | |
| 8,372,411 B2 | 2/2013 | Meinke et al. | |
| 8,381,729 B2 | 2/2013 | Freitag et al. | |
| 8,820,931 B2 | 9/2014 | Walsh et al. | |
| 2001/0025226 A1 | 9/2001 | Lavery | |
| 2002/0021411 A1 | 2/2002 | Wilson | |
| 2002/0080329 A1 | 6/2002 | Kasahara | |
| 2002/0099305 A1 | 7/2002 | Fukushima et al. | |
| 2003/0065636 A1 | 4/2003 | Peyrelevade | |
| 2003/0232015 A1 | 12/2003 | Brown et al. | |
| 2004/0019032 A1 | 1/2004 | North et al. | |
| 2004/0036838 A1* | 2/2004 | Podoleanu et al. | 351/206 |
| 2004/0141152 A1 | 7/2004 | Marino et al. | |
| 2004/0196432 A1 | 10/2004 | Su et al. | |
| 2004/0254154 A1 | 12/2004 | Ashton | |
| 2004/0260183 A1 | 12/2004 | Lambert et al. | |
| 2005/0001980 A1 | 1/2005 | Spector | |
| 2005/0041200 A1 | 2/2005 | Rich | |
| 2005/0105044 A1 | 5/2005 | Warden et al. | |
| 2005/0140981 A1 | 6/2005 | Waelti | |
| 2006/0077347 A1 | 4/2006 | Liang et al. | |
| 2006/0077348 A1 | 4/2006 | Gorin | |
| 2006/0092376 A1 | 5/2006 | Beak et al. | |
| 2006/0109423 A1 | 5/2006 | Wang | |
| 2006/0119858 A1 | 6/2006 | Knighton et al. | |
| 2006/0135859 A1 | 6/2006 | Iliff | |
| 2006/0158655 A1 | 7/2006 | Everett et al. | |
| 2006/0187462 A1 | 8/2006 | Srinivasan et al. | |
| 2006/0195076 A1 | 8/2006 | Blumenkranz et al. | |
| 2006/0257451 A1 | 11/2006 | Varner et al. | |
| 2007/0008116 A1 | 1/2007 | Bergman et al. | |
| 2007/0024868 A1 | 2/2007 | Izatt et al. | |
| 2007/0030450 A1 | 2/2007 | Liang et al. | |
| 2007/0032782 A1 | 2/2007 | Youssefi et al. | |
| 2007/0055222 A1 | 3/2007 | Hohla et al. | |
| 2007/0073113 A1 | 3/2007 | Squilla et al. | |
| 2007/0081165 A1 | 4/2007 | Kilic et al. | |
| 2007/0081166 A1 | 4/2007 | Brown et al. | |
| 2007/0153233 A1 | 7/2007 | Campin et al. | |
| 2007/0177104 A1 | 8/2007 | Lacombe et al. | |
| 2007/0195269 A1 | 8/2007 | Wei et al. | |
| 2007/0216909 A1 | 9/2007 | Everett et al. | |
| 2007/0273831 A1 | 11/2007 | Liang et al. | |
| 2007/0282313 A1 | 12/2007 | Huang et al. | |
| 2007/0287932 A1 | 12/2007 | Huang et al. | |
| 2007/0291228 A1 | 12/2007 | Huang et al. | |
| 2007/0291277 A1 | 12/2007 | Everett et al. | |
| 2008/0007694 A1 | 1/2008 | Wei et al. | |
| 2008/0106696 A1 | 5/2008 | Buckland et al. | |
| 2009/0141240 A1 | 6/2009 | Weitz et al. | |
| 2009/0153796 A1 | 6/2009 | Rabner | |
| 2010/0100238 A1* | 4/2010 | Torian | 700/233 |
| 2010/0110377 A1 | 5/2010 | Maloca et al. | |
| 2011/0299034 A1 | 12/2011 | Walsh et al. | |
| 2014/0275935 A1 | 9/2014 | Walsh et al. | |

FOREIGN PATENT DOCUMENTS

| | | |
|---|---|---|
| CN | 1593329 A | 3/2005 |
| CN | 200 980 154 Y | 11/2007 |
| CN | 201 491 234 U | 5/2010 |
| DE | 10 2005 05822 | 6/2007 |
| EP | 0697611 A | 2/1996 |
| EP | 1 775 545 | 4/2007 |
| EP | 1858402 | 11/2007 |
| EP | 1 864 608 A | 12/2007 |
| EP | 2124713 | 12/2009 |
| JP | S 57-29204 | 6/1982 |
| JP | S 57-153635 | 9/1982 |
| JP | 11 225958 A | 8/1999 |
| JP | 2004-528111 | 9/2004 |
| JP | 2005-083954 | 3/2005 |
| JP | 2005-531346 | 11/2005 |
| WO | WO 99/57507 | 11/1999 |
| WO | WO 02/088684 | 11/2002 |
| WO | WO 2004/002298 | 1/2004 |
| WO | WO 2006/078802 | 7/2006 |
| WO | WO 2007/065493 | 6/2007 |
| WO | WO 2007/139927 | 12/2007 |
| WO | WO 2007/142960 | 12/2007 |
| WO | WO 2008/101359 | 8/2008 |
| WO | WO 2009/095473 | 8/2009 |
| WO | WO 2009/120543 | 10/2009 |
| WO | WO 2009/120544 | 10/2009 |
| WO | WO 2009/128912 | 10/2009 |
| WO | WO 2009/131701 | 10/2009 |
| WO | WO 2010/009447 | 1/2010 |
| WO | WO 2010/009450 | 1/2010 |
| WO | WO 2010/117386 | 10/2010 |
| WO | WO 2014/158658 | 1/2015 |

OTHER PUBLICATIONS

Second Office Action in Chinese Application No. 200980119252.3, dated Jul. 25, 2013 in 4 pages.
Office Action in Chinese Application No. 200980119252.3, dated Aug. 29, 2012 in 6 pages.

(56) References Cited

OTHER PUBLICATIONS

Final Office Action in U.S. Appl. No. 13/054,481, dated Jul. 29, 2013, in 24 pages.
"STRATUS OCT™ Software version 4.0 Real Answers in Real Time." [Online] Jan. 2006, XP002530105 Retrieved from the Internet: URL: http://www.meditec.zeiss.com/88256DE3007B916B/0/C26634D0CFF04511882571B1005DECFD/$file/stratusoct_en.pdf>[retrieved on May 28, 2009] the whole document.
Bachmann, et al., Heterodyne Fourier domain optical coherence tomography for full range probing with high axial resolution; Optics Express; vol. 14; Issue No. 4; pp. 1487-1496, 2006.
Bigelow, et al., Compact multimodal adaptive-optics spectral-domain optical coherence tomography instrument for retinal imaging; J.Opt. Soc., Am. A.; vol. 24; Issue No. 5; pp. 1327-1336, 2007.
Bu, et al., Full-range parallel Fourier-domain optical coherence tomography using sinusoidal phase-modulating interferometry; J. Opt. A: Pure Appl. Opt.; No. 9; pp. 422-426, 2007.
Burgansky-Eliash, et al., Optical Coherence Tomography Machine Learning Classifiers for Glaucoma Detection: A Preliminary Study, Investigative Ophthalmology & Visual Science; vol. 46; No. 11; pp. 4147-4152, 2005.
Chang, et al.; New developments in optical coherence tomography for glaucoma, Curr Opin Ophthalmol; No. 19; pp. 127-135; 2008.
Drexler, et al., State-of-the-art retinal optical coherence tomography; Progress in Retinal and Eye Research; vol. 27; Issue 1; pp. 45-88; 2008.
Fernandez, Delineating Fluid-Filled Region Boundaries in Optical Coherence Tomography Images of the Retina; IEEE Transactions on Medical Imaging; vol. 24; Issue No. 8; pp. 929-945, 2005.
Ghosn, et al., Nondestructive Quantification of Analyte Diffusion in Cornea and Sclera Using Optical Coherence Tomography; investigative Ophthalmology & Visual Science; vol. 48, No. 6, pp. 2726-2733, 2007.
Guo et al., "En face optical coherence tomography" a new method to analyse structural changes of the optic nerve head in rat glaucoma, retrieved from the Internet: ,URL: http://www.ncbi.nlm.nih.gov/pmc/articles/PMC1772813/pdf/bjo08901210.pdf>, British Journal of Ophthalmology, 2005, vol. 89, Issue 9, pp. 1210-1216.
Huang, et al., Development and Comparison of Automated Classifiers for Glaucoma Diagnosis Using Stratus Optical Coherence Tomography; Investigative Ophthalmology & Visual Science; vol. 46; Issue No. 11; pp. 4121-4129, 2005.
International Preliminary Report of Patentability dated Jan. 18, 2011 for PCT Application No. PCT/US2009/051073 filed on Jul. 17, 2009.
International Preliminary Report of Patentability dated Oct. 11, 2011 for PCT Application No. PCT/US2009/059133 filed on Sep. 30, 2009.
International Preliminary Report on Patentability dated Jan. 18, 2011 for PCT Application No. PCT/US2009/051077 filed on Jul. 17, 2009.
International Preliminary Report on Patentability dated Sep. 28, 2010 for PCT Application No. PCT/US2009/037448 filed on Mar. 17, 2009.
International Preliminary Report on Patentability dated Sep. 28, 2010 for PCT Application No. PCT/US2009/037449 filed on Mar. 17, 2009.
International Search Report and Written Opinion Received in PCT /US2009/051077 Dated Oct. 13, 2009.
International Search Report and Written Opinion Received in PCT/US2009/051073 Dated Jan. 13, 2010.
International Search Report and Written Opinion Received in PCT/US2009/059133 Dated Jan. 21, 2010.
International Search Report and Written Opinion Received in PCT/US2009/037449 Dated Aug. 27, 2009.
International Search Report and Written Opinion Received in PCT/US2009/037448 Dated Dec. 6, 2009.
Japanese Office Action for Japanese Application No. JP 2011-501911, dated May 1, 2013 in 7 pages.
Keystone View; Computer Controlled vision Screeners. http://www.keystoneview.com?p=cv&id=39, 2 pages, 2003.
Koizumi et al: "Three-Dimensional Evaluation of Vitreonacular Traction and Epiretinal Membrane Using Spectral—Domain Optical Coherence Tomography" American Journal of Ophthalmology, Ophthalmic Publ, Chicago, IL, US, vol. 145, No. 3, Jan. 11, 2008, pp. 509-517 .el, right-hand column, last paragraph—p. 154, left-hand column.
Koozekanani, et al., Retinal Thickness Measurements from Optical Coherence Tomography Using a Markov Boundary Model. IEEE Transactions on Medical Imaging; vol. 20; No. 9; pp. 900-916, 2001.
Lavanya, et al, Screening for Narrow Angles in the Singapore Population: Evaluation of New Noncontact Screening Methods; vol. 115; Issue No. 10, pp. 1720-1727e2, 2008.
Manassakorn, et al., Comparison of Retinal Nerve Fiber Layer Thickness and Optic Disk Algorithms with Optical Coherence Tomography to Detect Glaucoma; Am J Ophthalmol; vol. No. 141; pp. 105-115; 2006.
Parikh, M.D., Diagnostic Capability of Optical Coherence Tomography (Stratus OCT 3) in Early Glaucoma; American Academy of Ophthalmology; pp. 2238-2243, 2007.
Prevent Blindness America. SureSight Vision Screener. Prevent Blindness Tri-State. http://wwww.preventblindness.org/tristate/suresight.html, 2 pages, 2006.
Sadda, Srinivas R., et al., Automated Detection of Clinically Significant Macular Edema by Grid Scanning Optical Coherence Tomography. American Academy of Ophthalmology, vol. 113, No. 7, pp. 1187 e.1-e.12, 2006.
Sarunic et al, "New Imaging Device Can Detect Glaucoma Risk", Duke Medicine News and Communications, 2008.
Stein, et al., A new quality assessment parameter for optical coherence tomography; Br J Ophthalmol; Issue No. 90; pp. 186-190; 2005.
Stereo Optical Co., Inc. The Optec® 5500/5500 P-Industry Standard for Visual Screening and Vision Testing Devices. http://www.stereooptical.com/html/optec-5500.html, 3 pages, 2007.
Stereo Optical Co., Inc. The Optec® Functional Vision Analyzer™—Contrast Sensitivity Tests with Two Glare Levels Under Four Testing Conditions. http://www.stereooptical.com/html/functional_vision_analyzer.html, 3 pages, 2007.
Supplementary European Search Report for Application No. 090798839.8, dated Jan. 30, 2012.
Topcon Optical Coherence Tomography 3D OCT-1000 Brochure, 7 pages, 2008.
Topcon Optical Coherence Tomography 3D OCT-1000 Mark II Brochure, 12 pages.
Vakhtin, et al, Common-path interferometer for frequency-domain optical coherence tomography; Applied Optics; vol. 42, Issue No. 34; pp. 6953-6958, 2003.
Vakhtin, et al., Demonstration of complex-conjugate-resolved harmonic Fourier-domain optical coherence tomography imaging of biological samples; Applied Optics; vol. 46; Issue No. 18; pp. 3870-3877, 2007.
Xu, et al., Anterior Chamber Depth and Chamber Angle and Their Associations with Ocular and General Parameters: The Beijing Eye Study. American Journal of Ophthalmology, vol. 145, pp. 929-936e1, 2008.
Yasuno, et al., One-shot-phase-shifting Fourier domain optical coherence tomography by reference wavefront tilting; Optics Express; vol. 12; Issue No. 25; pp. 6184-6191, 2004.
Zhang, et al., Full range polarization-sensitive Fourier domain optical coherence tomography; Optics Express; vol. 12; Issue No. 24; pp. 6033-6039, 2004.
Zhou et al., "Biometric measurement of the mouse eye using optical coherence tomography with focal plane advancement", *Vision Research*, 2008, vol. 48, pp. 1137-1143.
Bowd, C., et al., "Bayesian Machine Learning Classifiers for Combining Structural and Functional Measurements to Classify Healthy and Glaucomatous Eyes," Investigative Ophthalmology & Visual Science, Mar. 2008, 49(3): 945-953.
Boyer, K.L., et al. "Automatic Recovery of the Optic Nervehead Geometry in Optical Coherence Tomography," IEEE Transactions on Medical Imaging, May 2006, 25(5): 553-570.
Walsh, A. "3D-OCT in the Evaluation of Retinal Disease," The Highlights, 2006, 34(3): 9-10.

(56) References Cited

OTHER PUBLICATIONS

Walsh, A. M.D., "Next-generation OCT: What to Look for in a Fourier Domain OCT Instrument," Retinal Physician, pp. 1-6, May 1, 2007.
Topcon Medical Systems Recieves FDA Clearence to Market the 3D OCT-1000, the World's First Combination for Fourier Domain OCT and a Color Non-Mydriatic Retinal Camera, TOPCON Press Release Jul. 2, 2007, pp. 1-2.
"A New Level for Retinal Imaging: Topcon's 3D OCT-1000," Vision Care Product New Nov./Dec. 2007 pp. 1-2.
"Topcon Medical Systems Releases 3D OCT-1000 TrueMap™ Software Version 2.12," TOPCON Press Release Feb. 8, 2008, pp. 1-2.
Brochure for Optical Coherence Tomography 3D OCT-1000 MARK II, in 12 pages.
Brochure for Optical Coherence Tomography 3D OCT-1000, in 11 pages, Copyright 2008.
"3D OCT-1000 | TOPCON," Press Release Mar. 31, 2008, available from internet at http://www.topcon.co.jp/news/20080331-508.html, site visited Apr. 14, 2015.
Chinese Fourth Office Action, re CN Application No. 200980119252.3, dated Oct. 28, 2014.
European Exam Report, re EP Application No. 09 724 806.6, dated Aug. 20, 2012.
International Search Report and Written Opinion, re PCT/US2014/019150, mailed Dec. 4, 2014.
Preliminary Amendment for U.S. Appl. No. 12/111,894 dated Aug. 15, 2008.
Office Action for U.S. Appl. No. 12/111,894 dated Feb. 16, 2011.
Amendment for U.S. Appl. No. 12/111,894 dated May 16, 2011.
Final Office Action for U.S. Appl. No. 12/111,894 dated Aug. 19, 2011.
Amendment for U.S. Appl. No. 12/111,894 dated Nov. 21, 2011.
Preliminary Amendment in U.S. Appl. No. 13/054,481, dated Feb. 14, 2011.
Office Action for U.S. Appl. No. 13/054,481 dated Aug. 15, 2012.
Amendment for U.S. Appl. No. 13/054,481, dated Nov. 16, 2012.
Final Office Action for U.S. Appl. No. 13/054,481 dated Dec. 21, 2012.
Amendment for U.S. Appl. No. 13/054,481, dated May 2, 2013.
Amendment for U.S. Appl. No. 13/054,481, dated Jan. 28, 2014.
Preliminary Amendement for U.S. Appl. No. 14/472,161, dated Dec. 8, 2014.
Preliminary Amendment for U.S. Appl. No. 13/802,727, dated Jun. 24, 2013.
Notice of Reasons for Rejection for Japanese Appl. No. 2014-016709 dated Feb. 17, 2015.

* cited by examiner

| Eye Health Grades | | |
|---|---|---|
| | Left | Right |
| Macular Health | 25 | 65 |
| Optic Nerve Health | 75 | 80 |
| Clarity | 45 | 90 |
| Recommendations | | ABCD-EFGH |

① Within 2 weeks, see either
- Dr. John
  123 Main Street
  Los Angeles, CA or
- Dr. Bob
  456 Main Street
  Los Angeles, CA ② Within 6 months, see
- Dr. Ellie
  999 Main Street
  Los Angeles, CA See an eye doctor at least once per year

FIG. 11A

Eye Health Assesment

Scan Date:
Scan Time:
Scan Location:

RIGHT EYE

| | |
|---|---|
| Macula | 90 |
| Optic Nerve | 60 |
| Front of Eye | 30 |

LEFT EYE

| | |
|---|---|
| Macula | 10 |
| Optic Nerve | 90 |
| Front of Eye | 90 |

RECOMMENDATIONS

See one of these doctors within <u>2 weeks</u>

Retina specialist A, (XXX) XXX-XXXX, 9999 Eye Blvd. Gardena CA
    Retina specialist B, (XXX) XXX-XXXX, 9999 Eye Blvd. Gardena CA
    Retina specialist C, (XXX) XXX-XXXX, 9999 Eye Blvd. Gardena CA See one of these doctors within <u>2 months</u>

Anterior specialist A, (XXX) XXX-XXXX, 9999 Eye Blvd. Gardena CA
    Anterior specialist B, (XXX) XXX-XXXX, 9999 Eye Blvd. Gardena CA
    Anterior specialist C, (XXX) XXX-XXXX, 9999 Eye Blvd. Gardena CA Remember to see an eye doctor every year!

FIG. 11B

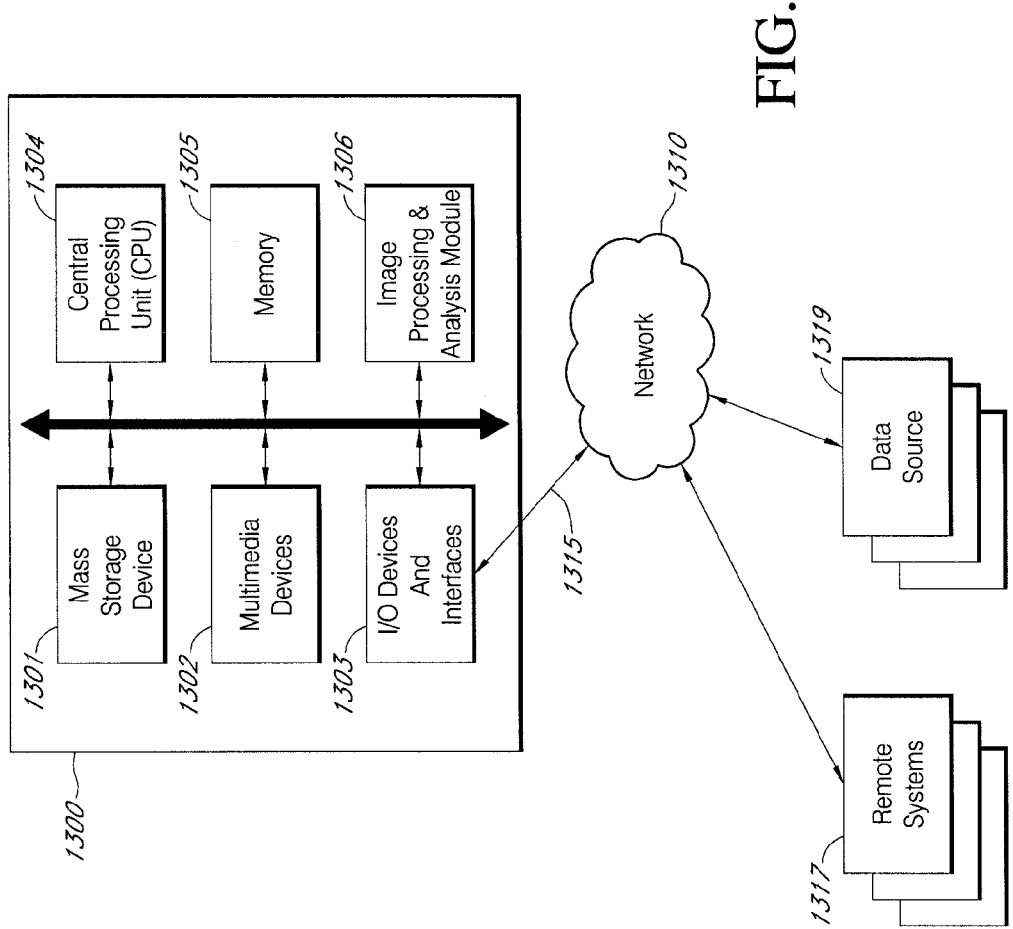

OPTICAL COHERENCE TOMOGRAPHY DEVICE, METHOD, AND SYSTEM

CROSS-REFERENCE TO RELATED APPLICATIONS

This application is a continuation of, and claims the benefit of, U.S. patent application Ser. No. 12/111,894, titled "OPTICAL COHERENCE TOMOGRAPHY DEVICE, METHOD, AND SYSTEM" and filed on Apr. 29, 2008, the disclosure of which is hereby incorporated by reference in its entirety. U.S. patent application Ser. No. 12/111,894 claims the benefit of U.S. Provisional Application No. 61/040,084, titled, "OPTICAL COHERENCE TOMOGRAPHY DEVICE, METHOD, AND SYSTEM," and filed Mar. 27, 2008, which is hereby incorporated by reference in its entirety, including without limitation, for example, the optical coherence tomography devices, methods, and systems disclosed therein.

BACKGROUND

1. Field

Embodiments of the invention relate to the field of optical coherence tomography and, in particular, to devices, systems, methods of utilizing such optical coherence tomography data to perform precision measurements on eye tissue for the detection of eye diseases.

2. Description of the Related Art

Many industrial, medical, and other applications exist for optical coherence tomography (OCT), which generally refers to an interferometric, non-invasive optical tomographic imaging technique offering millimeter penetration (approximately 2-3 mm in tissue) with micrometer-scale axial and lateral resolution. For example, in medical applications, doctors generally desire a non-invasive, in vivo imaging technique for obtaining sub-surface, cross-sectional and/or three-dimensional images of translucent and/or opaque materials at a resolution equivalent to low-power microscopes. Accordingly, in the coming years, it is projected that there will be 20 million OCT scans performed per year on patients. Most of these will probably occur in the field of ophthalmology. In current optical coherence tomography systems, doctors or other medical professionals administer the OCT scans in the doctors' medical office or medical facilities.

SUMMARY

Various embodiments of the present invention relate to the utilization of optical coherence tomography, which generally refers to an interferometric, non-invasive optical tomographic imaging technique, that can be used to detect and analyze, for example, eye tissue, and/or disease features, including but not limited to cystoid retinal degeneration, outer retinal edema, subretinal fluid, subretinal tissue, macular holes, drusen, or the like. For example, and in accordance with one aspect of the present invention, an optical coherence tomography instrument comprises an eyepiece for receiving at least one eye of a user; a light source that outputs light that is directed through the eyepiece into the user's eye; an interferometer configured to produce optical interference using light reflected from the user's eye; an optical detector disposed so as to detect said optical interference; electronics coupled to the detector and configured to perform a risk assessment analysis based on optical coherence tomography measurements obtained using said interferometer; and an output device electrically coupled to the electronics, and the output device may be configured to output the risk assessment to the user through the output device. Generally, the optical coherence tomography instruments, devices, systems, and methods disclosed herein can be self-administered, and the eyepiece can be a monocular system or a binocular system.

In accordance with another aspect of the present invention, an optical coherence tomography instrument comprises first and second oculars for receiving a pair of eyes of a user; a light source that outputs light that is directed through the first and second oculars to the user's eyes; an interferometer configured to produce optical interference using light reflected from the user's eye; an optical detector disposed so as to detect said optical interference; and electronics coupled to the detector and configured to provide an output to a user based on optical coherence tomography measurements obtained using said interferometer.

In other aspects of the present invention, an optical coherence tomography instrument comprises an eyepiece for receiving at least one eye of a user; a light source that outputs a beam that is directed through the eyepiece to the user's eye; an interferometer configured to produce optical interference using light reflected from the user's eye; an optical detector disposed so as to detect said optical interference; a electronics coupled to the detector and configured to automatically perform a diagnosis based on optical coherence tomography measurements obtained using said interferometer; and an output device electrically coupled to the electronics, said output device configured to output the diagnosis to the user through the output device.

In accordance with another aspect of the present invention, an optical coherence tomography instrument for providing self-administered disease screening, said instrument comprises an eyepiece for receiving at least one eye of a user; a light source that outputs a beam that is directed through the eyepiece to the user's eye; an interferometer configured to produce optical interference using light reflected from the user's eye; an optical detector disposed so as to detect said optical interference; a processor in communication with the detector and configured to identify one or more diseases that the user may manifest indications of based on optical coherence tomography measurements obtained using said interferometer; and an output device electrically coupled to the electronics, said output device configured to alert the user.

In other aspects of the present invention, an optical coherence tomography instrument comprises an eyepiece for receiving at least one eye of a user; at least one target display visible through said eyepieces; a light source that outputs light that is directed through the eyepiece to the user's eye; an interferometer configured to produce optical interference using light reflected from the user's eye; an optical detector disposed so as to detect said optical interference; and electronics coupled to the target display and said detector and configured to provide an output to a user based on optical coherence tomography measurements obtained using said interferometer, wherein said electronics is further configured to produce features on said target display of varying size and receive user responses to test a user's visual acuity.

In accordance with another aspect of the present invention, an optical coherence tomography instrument comprises an eyepiece for receiving at least one eye of a user; a light source that outputs light that is directed through the eyepiece to the user's eye; an interferometer configured to produce optical interference using light reflected from the user's eye; an optical detector disposed so as to detect said optical interference; electronics coupled to the detector and configured to provide an output to a user based on optical coherence tomography measurements; and a card reader configured to receive a card from said user, said card reader in communication with said electronics to transmit signals thereto to authorize said electronics to provide the output to said user.

In other aspects of the present invention, an optical coherence tomography instrument comprises an eyepiece for receiving at least one eye of a user; a light source that outputs light that is directed through the eyepiece to the user's eye; an interferometer configured to produce optical interference using light reflected from the user's eye; an optical detector disposed so as to detect said optical interference; electronics coupled to the detector and configured to provide an output to a user based on optical coherence tomography measurements obtained using said interferometer; memory that includes a list of healthcare providers; and an output device electrically coupled to the electronics to provide an output to said user, wherein said electronics is configured to access said memory to provide at least a portion of said list in said output to said user.

In accordance with another aspect of the present invention, an optical coherence tomography instrument comprises an eyepiece for receiving at least one eye of a user; a light source that outputs light that is directed through the eyepiece to the user's eye; an interferometer configured to produce optical interference using light reflected from the user's eye; an optical detector disposed so as to detect said optical interference; electronics coupled to the detector and configured to provide an output to a user based on optical coherence tomography measurements obtained using said interferometer; and an output device electrically coupled to the electronics and configured to provide an output to said user, wherein said electronics is configured to provide a recommended deadline for consulting a healthcare provider based on the patient's risk level of having certain types of diseases as determined using said optical coherence tomography measurements.

In other aspects of the present invention, an optical coherence tomography instrument comprises an eyepiece for receiving an eye of a user; a light source that outputs a light beam that is directed through the eyepiece to the user's eye; an interferometer configured to produce optical interference using light reflected from the user's eye; an optical detector disposed so as to detect said optical interference; an array of display elements visible to the user through the eyepiece, said array of display elements configured to display a display target at different locations across the array; and electronics in communication with said array of display elements and said detector, said electronics configured to use said position of said display target on said array of display elements to associate optical coherence tomography measurements with spatial locations.

In accordance with another aspect of the present invention, an optical coherence tomography instrument comprises an eyepiece for receiving a subject's eye; a light source that outputs light that is directed through the eyepiece to the subject's eye; an interferometer configured to produce optical interference using light reflected from the user's eye; an optical detector disposed so as to detect said optical interference; and memory including statistical information correlating optical coherence tomography measurements with risk of at least one disease; electronics coupled to the detector and configured to access said memory to compare data obtained based on optical coherence tomography measurements of said subject's eye using said interferometer with said statistical information to provide an assessment of said subject's risk of having said at least one disease.

In other aspects of the present invention, an optical coherence tomography instrument comprises an eyepiece for receiving an eye of a user; a light source that outputs light that is directed through the eyepiece to the user's eye; an adjustable optical element configured to alter the focus of the light directed into the user's eye; an interferometer configured to produce optical interference using light reflected from the user's eye; an optical detector disposed so as to detect said optical interference; electronics coupled to the detector and configured to provide an output to a user based on optical coherence tomography measurements obtained using said interferometer; and an output device electrically coupled to the electronics and configured to provide an output to said user, wherein said electronics is configured to adjust said optical element to focus said light using a signal from said detector.

For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIGS. 11A-11B illustrate possible embodiments of output reports generated by the optical coherence tomography device.

FIG. 13 is a block diagram schematically illustrating components in one embodiment of the computer system for an optical coherence tomography system described herein.

FIG. 15 is an illustration of RPE detection and RPE polynomial fit curvature, and the difference there between.

DETAILED DESCRIPTION

Figure 1:
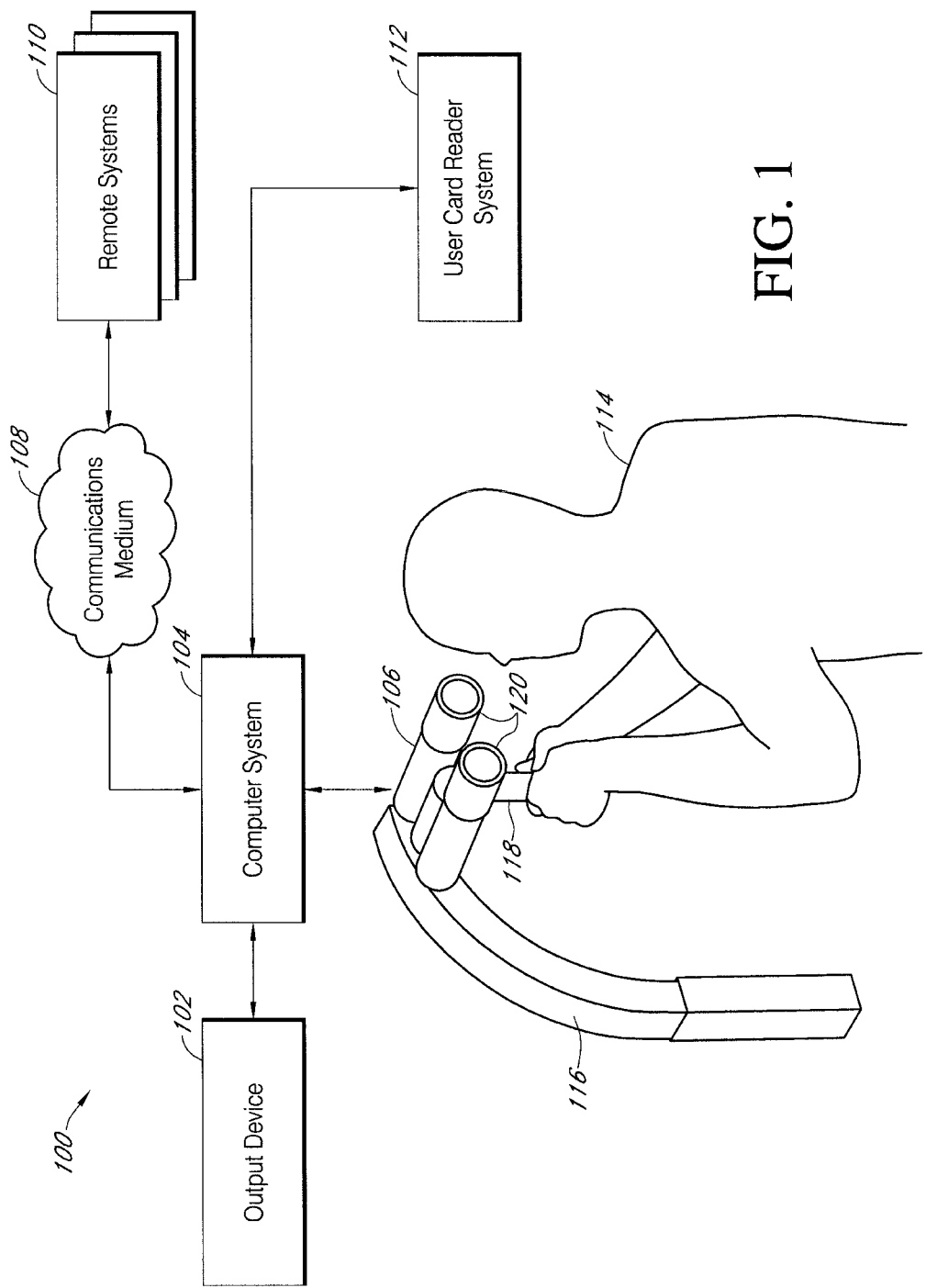
FIG. 1 is a schematic diagram of one embodiment of the optical coherence tomography system described herein.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described. The embodiments described herein make OCT screening more accessible to users thereby allowing for earlier detection and/or treatment of various diseases, ailments, or conditions, for example, maculopathy, glaucoma, or the like.

The terms "optical coherence tomography" and "OCT" generally refer to an interferometric technique for imaging samples, in some cases, with micrometer lateral resolution. This non-invasive optical tomographic imaging technique is used in ophthalmology to provide cross-sectional images of the eye, and more particularly the posterior of the eye, though it can also be used to image other samples or tissues in areas of the user's body.

Generally, OCT employs an interferometer. Light from a light source (for example, a broadband light source) is split (for example, by a beamsplitter) and travels along a sample arm (generally comprising the sample) and a reference arm (generally comprising a mirror). A portion of the light from the sample arm is reflected by the sample. Light is also reflected from a mirror in the reference arm. (Light from the test arm and the reference arm is recombined, for example by the beamsplitter.) When the distance travelled by light in the sample arm is within a coherence length of the distance travelled by light in the reference arm, optical interference occurs, which affects the intensity of the recombined light. The intensity of the combined reflected light varies depending on the sample properties. Thus, variations for the intensity of the reflectance measured are indications of the physical features of the sample being tested.

In time-domain OCT, the length of the reference arm can be varied (for example, by moving one or more reference mirrors). The reflectance observed as the reference arm distance changes indicates sample properties at different depths of the sample. (In some embodiments, the length of the sample arm is varied instead of or in addition to the variation of the reference arm length.) In frequency-domain OCT, the distance of the reference arm can be fixed, and the reflectance can then be measured at different frequencies. For example, the frequency of light emitted from a light source can be scanned across a range of frequencies or a dispersive element, such as a grating, and a detector array may be used to separate and detect different wavelengths. Fourier analysis can convert the frequency-dependent reflectance properties to distance-dependent reflectance properties, thereby indicating sample properties at different sample depths. In certain embodiments, OCT can show additional information or data than nonmydriatic color fundus imaging.

The term "A-scan" describes the light reflectivity associated with different sample depths. The term "B-scan" as used herein refers to the use of cross-sectional views of tissues formed by assembly of a plurality of A-scans. In the case of ophthalmology, light reflected by eye tissues is converted into electrical signals and can be used to provide data regarding the structure of tissue in the eye and to display a cross-sectional view of the eye. In the case of ophthalmology, A-scans and B-scans can be used, for example, for differentiating normal and abnormal eye tissue or for measuring thicknesses of tissue layers in the eyes.

In ophthalmic instances, an A-scan can generally include data from the cornea to the retina, and a B-scan can include cross-sectional data from a medial border to a lateral border of the eye and from the cornea to the retina. Three-dimensional C-scans can be formed by combining a plurality of B-scans.

As used herein the terms "user" or "patient" may be used interchangeably, and the foregoing terms comprise without limitation human beings, whether or not under the care of a physician, and other mammals.

The terms "eye scan," "scanning the eye," or "scan the eyes," as used herein, are broad interchangeable terms that generally refer to the measurement of any part or substantially all of the eye, including but not limited to the cornea, the retina, the eye lens, the iris, optic nerve, or any other tissue or nerve related to the eye.

The terms "risk assessment" and "diagnosis," may be used in the specification interchangeably although the terms have different meanings. The term "risk assessment" generally refers to a probability, number, score, grade, estimate, etc. of the likelihood of the existence of one or more illnesses, diseases, ailments, or the like. The term "diagnosis" generally refers to a determination by examination and/or tests the nature and circumstances of an illness, ailment, or diseased condition.

The disclosure herein provides various methods, systems, and devices for generating and utilizing optical coherence tomography image data to perform precision measurements on retinal tissue for the detection of disease features, and generating a risk assessment and/or diagnosis based on data obtained by optical coherence tomography imaging techniques. These methods, systems and devices may employ, in some embodiments, a statistical analysis of the detected disease features obtained by optical coherence tomography imaging techniques. Such methods, systems, and devices can be used to screen for diseases.

With reference to FIG. 1, there is illustrated a block diagram depicting one embodiment of the optical coherence tomography system. In one embodiment, computer system 104 is electrically coupled to an output device 102, a communications medium 108, and a user card reader system 112. The communications medium 108 can enable the computer system 104 to communicate with other remote systems 110. The computer system 104 may be electrically coupled to main body 106, which the user 114 positions near or onto the user's eyes. In the illustrated example, the main body 106 is a binocular system (for example, has a two oculars or optical paths for the eyes providing one view for one eye and another view for another eye, or the like) configured to scan two eyes without repositioning the oculars with respect to the head of the patient, thereby reducing the time to scan a patient. In some embodiments, the eyes are scanned simultaneously using a scanner (for example, galvanometer), which provides interlaces of measurements from both eyes. Other embodiments are possible as well, for example, the binocular system or a two ocular system having two respective optical paths to the two eyes can be configured to scan the eyes in series, meaning one eye first, and then the second eye. In some embodiments, serial scanning of the eyes comprises scanning a first portion of the first eye, a first portion of the second eye, a second portion the first eye, and so on. Alternatively, the main body 106 can comprise a monocular system or one ocular system or optical path to the eye for performing eye scans.

Referring to FIG. 1, the user 114 can engage handle 118 and position (for example, up, down, or sideways) the main body 106 that is at least partially supported and connected to a zero gravity arm 116, and accordingly the system 100 has no chin rest. In some embodiments, this configuration can introduce positioning error due to movement of the mandible. When the main body 106 is in such a position, the distance between the outermost lens (the lens closest to the user) and the user's eye can range between 10 mm and 30 mm, or 5 mm and 25 mm, or 5 mm and 10 mm. The close proximity of the lens system to the user's eyes increases compactness of the system, reduces position variability when the patient places his eyes (for example, orbital rims) against the man body, and increases the viewing angle of the OCT apparatus when imaging through an undilated pupil. Accordingly, the main body 106 can also comprise eyecups 120 (for example, disposable eyecups) that are configured to contact the user's eye socket to substantially block out ambient light and/or to at least partially support the main body 106 on the eye socket of the user 114. The eyecups 120 have central openings (for example, apertures) to allow passage of light from the light source in the instrument to the eyes. The eyecups 120 can be constructed of paper, cardboard, plastic, silicon, metal, latex, or a combination thereof. The eyecups 120 can be tubular, conical, or cup-shaped flexible or semi-rigid structures with openings on either end. Other materials, shapes and designs are possible. In some embodiments, the eyecups 120 are constructed of latex that conforms around eyepiece portions of the main body 106. The eyecups 120 are detachable from the main body 106 after the eye scan has been completed, and new eyecups 120 can be attached for a new user to ensure hygiene and/or to protect against the spread of disease. The eyecups 120 can be clear, translucent or opaque, although opaque eyecups offer the advantage of blocking ambient light for measurement in lit environments.

The main body 106 may comprise one or more eyepieces, an interferometer, one or more target displays, a detector and/or an alignment system. The optical coherence tomography system may comprise a time domain optical coherence tomography system and/or a spectral domain optical coherence tomography system. Accordingly, in some embodiments, the main body 106 comprises a spectrometer, (for example, a grating) and a detector array. The main body may, in some embodiments, comprise signal processing component (for example, electronics) for performing, for example, Fourier transforms. Other types of optical coherence tomography systems may be employed.

Figure 2:
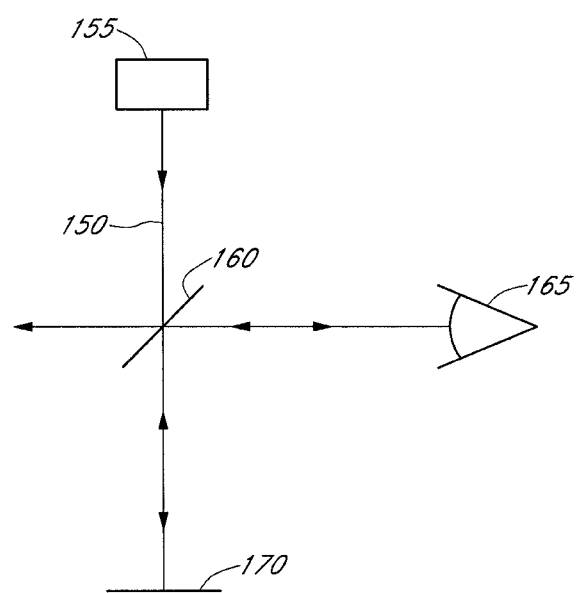
FIG. 2 is a schematic diagram of one embodiment of an interferometer arranged to perform measurements of an eye.

FIG. 2 shows a diagram of an example optical coherence tomography system. Light 150 is output from a light source 155. The light source 155 may comprise a broadband light source, such as a superluminescent diode or a white light source. (Alternatively, light emitted from the light source 155 may vary in frequency as a function of time.) The light 150 may comprise collimated light. In one embodiment, light 150 from the light source 155 is collimated with a collimating lens. The light is split at beamsplitter 160. Beamsplitters, as described herein, may comprise without limitation a polarization-based beamsplitter, a temporally based beamsplitter and/or a 50/50 beamsplitter or other devices and configurations. A portion of the light travels along a sample arm, directed towards a sample, such as an eye 165 of a user 114. Another portion of the light 150 travels along a reference arm, directed towards a reference mirror 170. The light reflected by the sample and the reference mirror 170 are combined at the beamsplitter 160 and sensed either by a one-dimensional photodetector or a two-dimensional detector array such as a charge-coupled device (CCD) or complementary metal-oxide-semiconductor (CMOS). A two-dimensional array may be included in a full field OCT instrument, which may gather information more quickly than a version that uses a one dimensional photodetector array instead. In time-domain OCT, the length of the reference arm (which may be determined in part by the position of the reference mirror 170) may be varying in time.

Whether interference between the light reflected by the sample and the light reflected by the reference mirror/s occurs will depend on the length of the reference arm (as compared to the length of the test arm) and the frequency of the light emitted by the light source. High contrast light interference occurs between light travelling similar optical distances (for example, (differences less than a coherence length). The coherence length is determined by the bandwidth of the light source. Broadband light sources correspond to smaller coherence lengths.

In time-domain OCT, when the relative length of the reference and sample arms varies over time, the intensity of the output light may be analyzed as a function of time. The light signal detected results from light rays scattered from the sample that interfere constructively with light reflected by the reference mirror/s. Increased interference occurs, however, when the lengths of the sample and reference arms are approximately similar (for example, within about one coherence length in some cases). The light from the reference arm, therefore, will interfere with light reflected from a narrow range of depths within the sample. As the reference (or sample) arms are translated, this narrow range of depths can be moved through the thickness of the sample while the intensity of reflected light is monitored to obtain information about the sample. Samples that scatter light will scatter light back that interferes with the reference arm and thereby produce an interference signal. Using a light source having a short coherence length can provide increased to high resolution (for example, 0.1-10 microns), as the shorter coherence length yields a smaller range of depths that is probed at a single instant in time.

In various embodiments of frequency-domain optical coherence tomography, the reference and sample arms are fixed. Light from a broadband light source comprising a plurality of wavelengths is reflected from the sample and interfered with light reflected by the reference mirror/s. The optical spectrum of the reflected signal can be obtained. For example, the light may be input to a spectrometer or a spectrograph comprising, for example, a grating and a detector array, that detects the intensity of light at different frequencies.

Fourier analysis performed, for example, by a processor may convert data corresponding to a plurality of frequencies to that corresponding to a plurality of positions within the sample. Thus, data from a plurality of sample depths can be simultaneously collected without the need for scanning of the reference arm (or sample) arms. Additional details related to frequency domain optical coherence tomography are described in Vakhtin et al., (Vakhtin A B, Kane D J, Wood W R and Peterson K A. "Common-path interferometer for frequency-domain optical coherence tomography," Applied Optics. 42(34), 6953-6958 (2003)).

Other methods of performing optical coherence tomography are possible. For example, in some embodiment of frequency domain optical coherence tomography, the frequency of light emitted from a light source varies in time. Thus, differences in light intensity as a function of time relate to different light frequencies. When a spectrally time-varying light source is used, a detector may detect light intensity as a function of time to obtain optical spectrum of the interference signal. The Fourier transform of the optical spectrum may be employed as described above. A wide variety of other techniques are also possible.

Figure 3A:
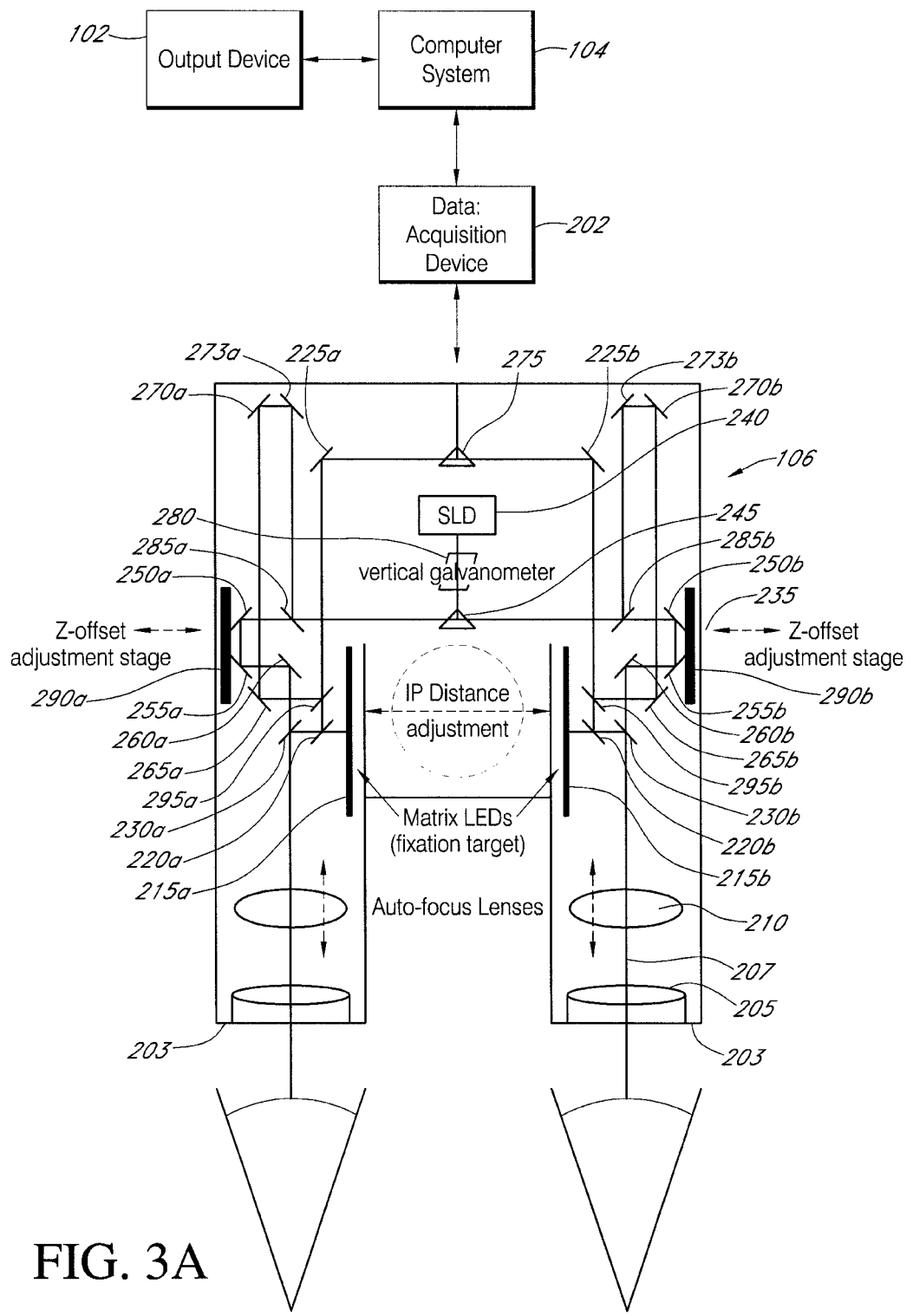
FIG. 3A is a schematic diagram of one embodiment of an OCT system comprising a main body configured to conveniently interfere with a person's eyes, the main body being in communication with various systems as described herein.

FIG. 3A shows one configuration of main body 106 comprising an optical coherence tomography system and an alignment system. Other optical coherence tomography systems and/or alignment systems may be included in place of or in addition to the systems shown in FIG. 3A. As shown, the main body 106 can include two eyepieces 203, each eyepiece configured to receive an eye from a user 114. In other embodiments, the main body 106 includes only one eyepiece 203.

FIG. 3A shows one representative embodiment of an optical coherence tomography system. Light from a light source 240 may propagate along a path that is modulated, for example, vertically and/or horizontally by one or more beam deflectors 280. A galvanometer may be used for this purpose. The galvanometer 280 can control the horizontal and/or vertical location of a light beam from the light source 240, thereby allowing a plurality of A-scans (and thus one or more B-scan and/or a C-scan) to be formed.

The light from the light source 240 is split at beamsplitter 245. In some embodiments, beamsplitter 245 is replaced by a high frequency switch that uses, for example, a galvanometer, that directs about 100% of the light towards mirror 250a for about ½ of a cycle and then directs about 100% of the light towards mirror 250b for the remainder of the cycle. The light source 240 may include a broadband light source, such as a superluminescent light-emitting diode. Light split at the beamsplitter 245 is then split again at beamsplitter 285a or 285b to form a reference arm and a sample arm. A first portion of the light split at beamsplitter 285a or 285b is reflected by reference mirrors 273a or 273b, reference mirrors 270a or 270b, and reference mirrors 265a or 265b. A second portion of the light split at beamsplitter 285a or 285b is reflected by mirror 250a or 250b, by mirror 255a or 255b and by mirror 260a or 260b. Mirrors 255a or 255b and mirrors 250a and 250b are connected to a Z-offset adjustment stage 290b. By moving the position of the adjustment stage 290a or 290b, the length of the sample arm is adjusted. Thus, the adjustment stage 290a or 290b can adjust the difference between the optical length from the light source 240 to a portion of the sample and the optical length from the light source 240 and the reference mirror 270a or 270b and/or reference mirror 273a or 273b. This difference can be made small, for example, less than a coherence length, thereby promoting for optical interference to occur. In some embodiments, the positions of one or more reference mirrors (for example, reference mirror 270a or 270b and reference mirror 273a or 273b) are movable in addition to or instead of the adjustment stage being movable. Thus, the length of the reference arm and/or of the sample arm may be adjustable. The position of the adjustment stages 290a and/or 290b may be based on the signals from the device, as described in more detail below.

The light reflected by mirror 260a or 260b is combined with light from display 215a or 215b at beamsplitter 230a or 230b. The displays 215a and 215b may comprise one or more light sources, such as in an emissive display like an array of matrix LEDs. Other types of displays can be used. The display can display targets of varying shapes and configurations, including a bar and/or one or more dots. A portion of the optical path from the light source 240 to the eye may be coaxial with a portion of the path from the displays 215a and 215b to the eye. These portions may extend though the eyepiece. Accordingly, a light beam from the light source 240 is coaxial with a light beam from the displays 215a and 215b such that the eyes can be positioned and aligned with respect to the eyepieces using the displays.

Figure 3B:
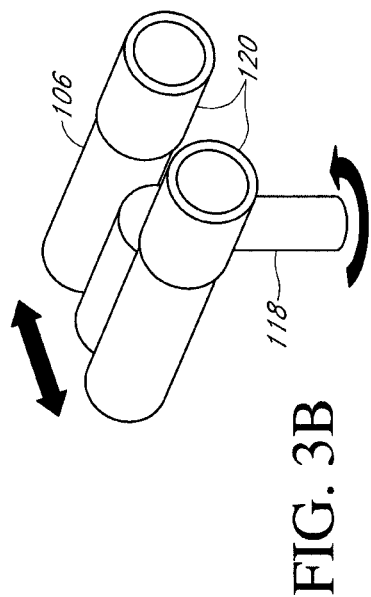
FIG. 3B is a perspective view schematically illustrating an embodiment of the main body shown in FIG. 3A.

As described in greater detail below, for example, the user 114 may use images from the displays in order to adjust interpupillary distance. In various embodiments, for example, proper alignment of two images presented by the displays may indicate that the interpupillary distance is appropriately adjusted. Thus, one or more adjustment controls 235 may be used to adjust the distance between the display targets 215a and 215b and/or between the eyepieces 203. The adjustment controls 235 may be provided on the sides of the main body 106 or elsewhere. In certain embodiments, the adjustment control 204 may comprise a handle on the main body 106, as shown in FIG. 3B. In this embodiment, rotation of the adjustment control 204 may increase or decrease the interpupillary distance.

The combined light (that is reflected by mirror 260a or 260b and that comes from display 215a or 215b) is focused by adjustable powered optics (for example, lens) 210 possibly in conjunction with optical element 205. The adjustable optics 210 may comprise a zoom lens or lens system that may be have, for example, a focal length and/or power that is adjustable. The adjustable optics 210 may comprise be part of an auto-focus system or may be manually adjusted. The adjustable optics 210 may provide optical correction for those in need of such correction (for example, a user whose glasses are removed during testing). The position of the powered optics 210 may be based on the signals obtained from the device, as described in more detail below. The focused light then travels through eyepiece windows or lens 205, positioned at a proximal end of the eyepiece 203, towards the eye of a user 114. In the case where a lens 205 is includes, this lens 205 may contribute to focusing of the light into the eye.

This light focused into the eye may be scattered by tissue or features therein. A portion of this scattered light may be directed back into the eyepiece. Lens 205 may thus receive light 207 reflected from the user's eye, which travels through the powered optics 210, reflects off of the beamsplitter 230a or 230b towards beamsplitter 220a or 220b, which reflects the light towards mirrors 295a or 295b. At 295a or 295b, light reflected by the sample interferes with light in the reference arm (path between beamsplitter 285a or 285b and beamsplitter 295a or 295b that includes mirrors 273a or 273b and 270a or 270b). (Accordingly, the sample arm includes the optical path between beamsplitter 285a or 285b and beamsplitter 295a or 295b that includes mirrors 250a or 250b and 255a or 255b and the sample or eye.) The light is then reflected by mirror 225a or 225b towards switch 275. In some embodiments, the switch 275 comprises a switchable deflector that switches optical paths to the first or second eye to collect data from the respective eye to be sent to the data acquisition device 202. The switch may comprise a low-frequency switch, such that all data to be collected from one eye is obtained before the data is collected from the other eye. Alternatively, the switch may comprise a high-frequency switch, which may interlace data collected from each eye.

The instrument may be configured differently. For example, a common reference path may be used for each eye. In some embodiments, the reference arm includes one or more movable mirrors to adjust the optical path length difference between the reference and sample arms. Components may be added, removed, or repositioned in other embodiments. Other techniques, may be used.

Although not shown, for example, polarizers and polarizing beamsplitters may be used to control the propagation of light through the optical path in the optical system. Other variations are possible. Other designs may be used.

In some embodiments, an A-scan may be formed in the time domain. In these instances, the Z-offset adjustment stage and corresponding mirror 255a or 255b and mirror 255a or 255b may change positions in time. Alternatively, reference mirrors 270a and 270b and reference mirrors 273a and 273b or other mirrors in the reference or sample arms may be translated. The combined light associated with various mirror positions may be analyzed to determine characteristics of an eye as a function of depth. In other embodiments, an A-scan may be formed in the spectral domain. In these instances, the frequencies of the combined light may be analyzed to determine characteristics of an eye as a function of depth. Additionally, one or more galvanometers 280 can control the horizontal and/or vertical location of the A-scan. Thus, a plurality of A-scans can be obtained to form a B-scan and/or a C-scan.

Light output from the structure 275 can be input into a data acquisition device 202, which may comprise, for example, a spectrometer or a light meter. A grating may be in the main body 106. The data acquisition device 202 is coupled to a computer system 104, which may present output based on scans to the user 114. The output device may include a monitor screen, in which output results are displayed. The output device may include a printer, which prints output results. The output device may be configured to store data on a portable medium, such as a compact disc or USB drive, or a custom portable data storage device.

In some embodiments, the computer system 104 analyzes data received by the data acquisition device 202 in order to determine whether one or more of the adjustment stages 290a and/or 290b and/or the powered optics 210 should be adjusted. In one instance, an A-scan is analyzed to determine a position (for example, a coarse position) of the retina such that data on the retina may be obtained by the instrument. In some embodiments, each A-scan comprises a plurality of light intensity values, each associated with a different depth into the sample. The A-scan may be obtained, in some embodiments, by translating the Z adjustment stage 290a or 290b. Likewise, the A-scan comprises values of reflected signal for obtained for different location of Z adjustment stage. The retina reflects more light than other parts of the eye, and thus, it is possible to determine a position of the adjustment stage 290a or 290b that effectively images the retina by assessing what depths provide an increase in reflected intensity. In some embodiments, the Z adjustment stage may be translated and the intensity values may be monitored. An extended peak in intensity for a number of Z adjustment stage positions may correspond to the retina. A variety of different approaches and values may be monitored to determine the location of the retina. For example, multiple A-scans may be obtained at different depths and the integrated intensity of each scan may be obtained and compared to determine which depth provided a peak integrated intensity. In certain embodiments, intensity values within an A-scan can be compared to other values within the A-scan and/or to a threshold. The intensity value corresponding to the preferred location may be greater than a preset or relative threshold and/or may be different from the rest of the intensity values, (for example, by more than a specified number of standard deviations). A wide variety of approaches may be employed.

After the positions of the adjustment stages 290a and 290b have been determined, subsequent image analysis may be performed to account for vibration or movement of the user's head, eyes or retinas relative to the light source 240. A feedback system such as a closed loop feedback system may be employed in effort to provide a more stabilized signal in the presence of such motion. The optical coherence tomography signal may be monitored and feedback provided to, for example, one or more translation stages to compensate for such vibration or movement. In some embodiments, subsequent image analysis may be based on initial image and/or detect changes in image characteristics. For example, the image analysis may determine that the brightest pixel within an A-scan has moved 3 pixels from a previous scan. The adjustment stage 290a or 290b may thus be moved based on this analysis. Other approaches may be used.

In some instances, optical coherence tomography signals are used to adjust the powered optics 210 to provide for increased or improved focus, for example, when a patient needs refractive correction. Many users/patients, for example, may wear glasses and may be tested while not wearing any glasses. The powered optics 210 may be adjusted based on reflected signal to determine what added correction enhances signal quality or is otherwise an improvement. Accordingly, in some embodiments, a plurality of A-scans is analyzed in order to determine a position for the powered optics 210. In some instances, a plurality of A-scans is analyzed in order to determine a position for the powered optics 210. In some embodiments, this determination occurs after the position of the adjustment stage 290a or 290b has been determined. One or more A-scans, one or more B-scans or a C-scan may be obtained for each of a plurality of positions of the powered optics 210. These scans may be analyzed to assess, for example, image quality. The position of the powered optics 210 may be chosen based on these image quality measures.

The image quality measure may include a noise measure. The noise measure may be estimated based on the distribution of different intensity levels of reflected light within the scans. For example, lower signals may be associated with noise. Conversely, the highest signals may be associated with a saturated signal. A noise measure may be compared to a saturation measure as in signal to noise ratios or variants thereof. The lowest reflectivity measured (referred to as a low measure or low value) may also be considered. In some embodiments, the positions of the adjustment stages 290a and/or 290b and/or the powered optics 210 is determined based upon a signal-to-noise measure, a signal strength measure, a noise measure, a saturation measure, and a low measure. Different combinations of these parameters may also be used. Values obtained by integrating parameters over a number of positions or scans, etc., may also be used. Other parameters as well as other image quality assessments may also be used.

In one embodiment, a noise value is estimated to be a reflected light value for which approximately 75% of the measured reflected light is below and approximately 25% of the measured reflected light is above. The saturation value is estimated to be a reflected light value for which approximately 99% of the measured reflected light is below and approximately 1% of the measured reflected light is above. A middle value is defined as the mean value of the noise value and the saturation value. An intensity ratio is defined as the difference between the saturation value and the low value divided by the low value multiplied by 100. A tissue signal ratio is defined as the number of reflected light values between the middle value and the saturation value divided by the number of reflected light values between the noise value and the saturation value. A quality value is defined as the intensity ratio multiplied by the tissue signal ratio. Additional details are described, for example, in Stein D M, Ishikawa H, Hariprasad R, Wollstein G, Noecker R J, Fujimoto J G, Schuman J S. A new quality assessment parameter for optical coherence tomography. Br. J. Ophthalmol. 2006; 90; 186-190. A variety of other approaches may be used to obtain a figure of merit to use to measure performance and adjust the instrument accordingly.

In the case of adjusting the adjustable power optics, 210, in some embodiments, a plurality of positions are tested. For example, the powered optics may be continuously moved in defined increments towards the eyes for each scan or set of scans. Alternatively, the plurality of positions may depend on previously determined image quality measures. For example, if a first movement of the powered optics 210 towards the eye improved an image quality measure but a subsequent second movement towards the eye decreased an image quality measure, the third movement may be away from the eye. Accordingly, optical power settings may be obtained that improve and/or maintains an improved signal. This optical power setting may correspond to optical correction and increase focus of the light beam in the eye, for example, on the retina, in some embodiments.

As described above, various embodiments employ an arrangement wherein a pair of oculars is employed. Accordingly, such adjustments, may be applied to each of the eyes as a user may have eyes of different size and the retina may located at different depths and thus a pair of z adjust stages may be used in some embodiments. Similarly, a user may have different prescription optical correction for the different eyes. A variety of arrangements may be employed to accommodate such needs. For example, measurements and/or adjustments may be performed and completed on one eye and subsequently performed and completed the other eye. Alternatively, the measurements and/or adjustments may be performed simultaneously or interlaced. A wide variety of other variations are possible.

Figure 4:
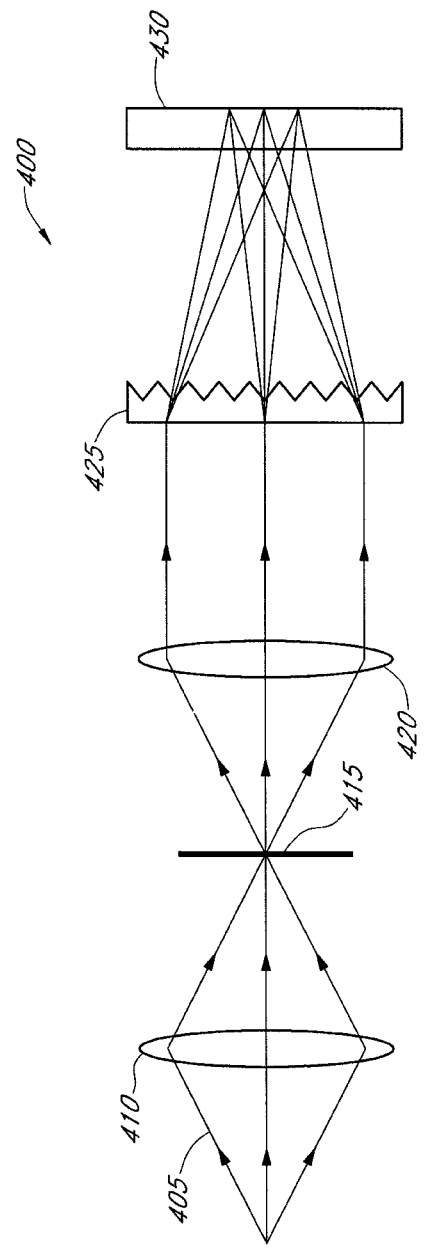
FIG. 4 is schematic diagram of one embodiment of a spectrometer used to analyze data from an interferometer used for OCT.

FIG. 4 shows a diagram of a spectrometer 400 that can be used as a data acquisition device 202 for a frequency domain OCT system. Light 405 input into the spectrometer 400 is collected by collecting lens 410. The collected light then projects through a slit 415, after which it is collimated by the collimating lens 420. The collimated light is separated into various spectral components by a grating 425. The grating 425 may have optical power to focus the spectral distribution onto an image plane. Notably, other separation components, such as a prism may be used to separate the light. The separated light is then directed onto a detector array by focusing lens 430, such that spectral components of each frequency from various light rays are measured.

A wide variety of OCT designs are possible. For example, frequency can be varied with time. The reference and sample arms can overlap. In some embodiments, a reference arm is distinct from a sample arm, while in other embodiments, the reference arm and sample arm are shared. See, for example, Vakhtin A B, Kane D J, Wood W R and Peterson K A. "Common-path interferometer for frequency-domain optical coherence tomography," Applied Optics. 42(34), 6953-6958 (2003). The OCT arrangements should not be limited to those described herein. Other variations are possible.

Figure 5:
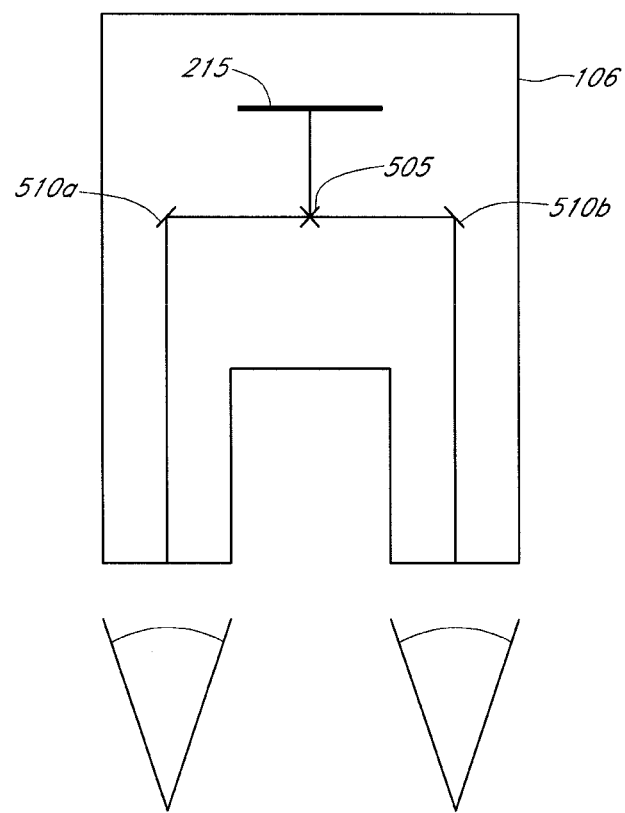
FIG. 5 is a schematic diagram of the main body of an OCT system comprising a single display for presenting a display target to a patient.

In some embodiments, as shown in FIG. 5, the main body 106 includes only a single display target 215. Light from the display target 215 is split at an x-prism 505. Notably, other optical devices that split the source light into a plurality of light rays may be used. This split light is reflected at mirror 510a or 510b and directed towards the user 114.

Figure 6:
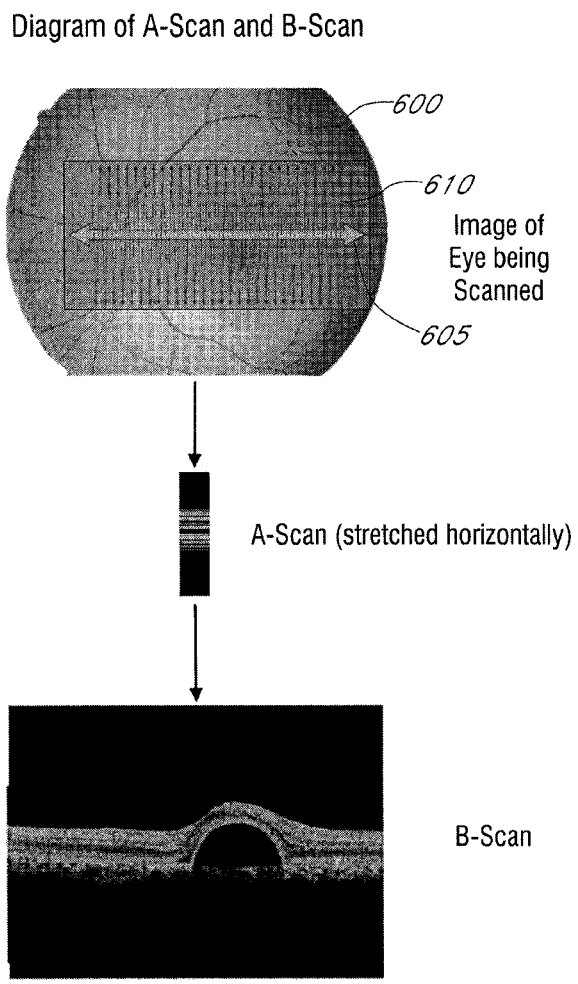
FIGS. 6A-6C are schematic diagrams illustrating the use of optical coherence tomography to scan retinal tissue to generate A-scans and B-scans.

The user may be directed to fixate on a display target 215 while one or more galvanometers 280 move light from the light source 240 to image an area of tissue. In some embodiments, the display targets 215 are moved within the user's field of vision while an area of tissue is imaged. For example, in FIG. 6A, a display target 215 may be moved horizontally (for example, in the medial-lateral direction), such that a patient is directed to look from left to right or from right to left. Meanwhile, a vertical scanner (for example, galvanometer) allows the vertical location (for example, in the superior-inferior) of the sample scanning to change in time. FIG. 6 shows an eye, which is directed to move in the horizontal direction 605. Due to the vertical scanner, the scanned trajectory 610 covers a large portion of the eye 600. Scanning in the vertical and horizontal directions can produce a C-scan. In some embodiments, continuous and/or regularly patterned A-scans are combined to form a full scan for example, B-scan or C-scan. In other embodiments, discrete and/or random A-scans are combined to form the full scan. Systems configured such that users 114 are directed to move their eyes throughout a scan may include fewer scanners than comparable systems configured such that users 114 keep their eyes fixated at a stationary target. For example, instead of a system comprising both a vertical and a horizontal scanner, the user 114 may move his eyes in the horizontal direction, thereby eliminating the need for a horizontal scanner.

FIG. 6B shows an example of an A scan. The A scan comprises the signal strength (indicated by the brightness) as a function of depth for one horizontal and vertical position. Thus, an A-scan comprises a plurality of intensity values corresponding to different anterior-posterior positions. A plurality of A scans form a B scan. FIG. 6C shows a B-scan, in which the largest portion of the bright signal corresponds to retinal tissue and the elevated region under the retina corresponds to diseased tissue within the eye.

Figure 7:
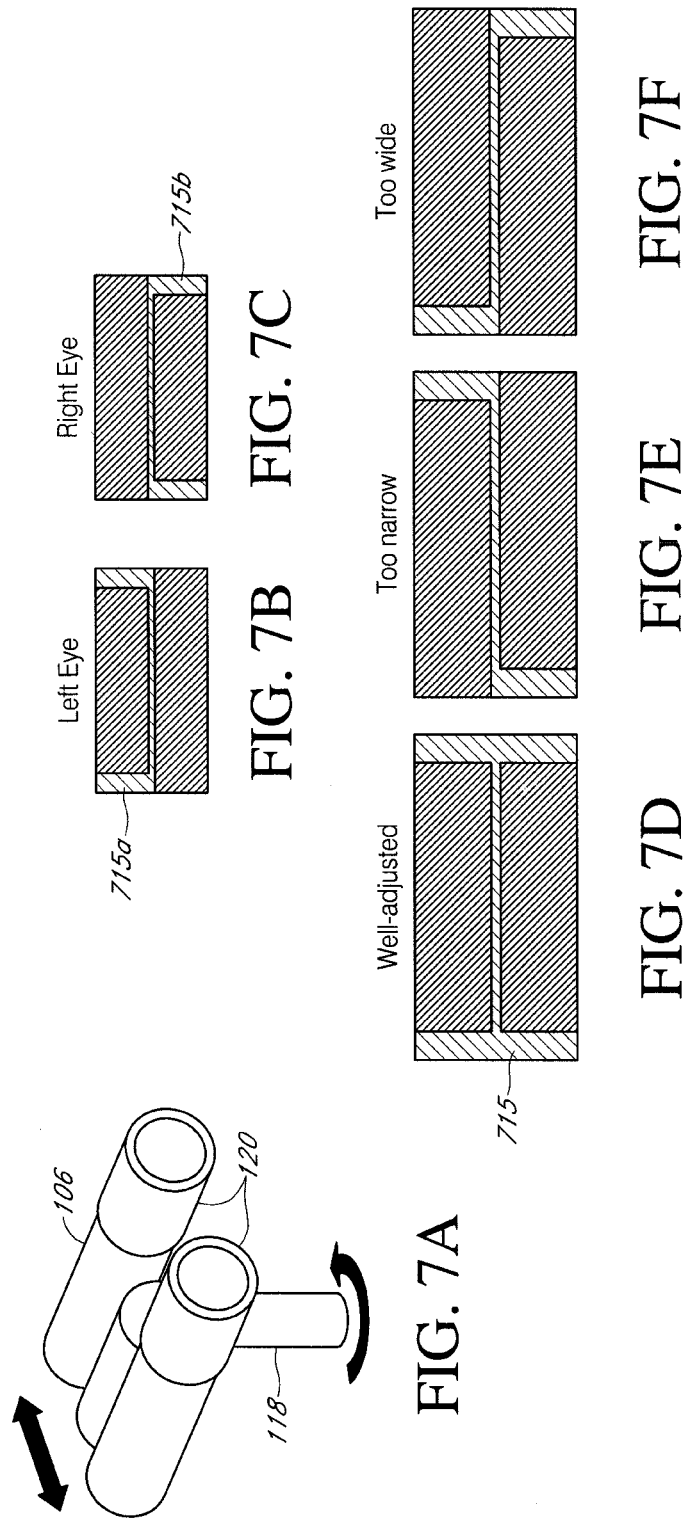
FIGS. 7A-7F are schematic diagrams illustrating embodiments for adjusting and/or calibrating interpupillary distance.

With reference to FIG. 7A, there is illustrated an enlarged view depicting an embodiment of the main body 106 that is configured with a handle 118 for adjusting the eyepieces to conform to the user's interpupillary distance. In the illustrative embodiment, the main body 106 comprises a left eyepiece 712 and a right eyepiece 714 wherein each is connected to the other by interpupillary distance adjustment device 718. The interpupillary distance adjustment device 718 is coupled to the handle 118, wherein the handle 118 is configured to allow the user to engage the handle 118 to adjust the distance between the left and right eyepieces 712, 714 to match or substantially conform to the interpupillary distance between the eyes of the user.

Referring to FIG. 7A, the user can rotate, turn, or twist the handle 118 to adjust the distance between the left and right eyepieces 712, 714 so as to match or substantially conform to the interpupillary distance between the eyes of the user. Alternatively, the handle 118 can be configured to move side to side to allow the user to adjust the distance between the left and right eyepieces 712, 714. Additionally, the handle 118 can be configured to move forward and backward to allow the user to adjust the distance between the left and right eyepieces 712, 714. In the alternative, the handle 118 can be configured to move up and down to allow the user to adjust the distance between the left and right eyepieces 712, 714. In another embodiment, the distance between the left and right eyepieces 712, 714 can be adjusted and/or controlled by a motor activated by the user. Alternatively, the motor can be configured to be controlled by computer system 104 to semi-automatically position the left and right eyepieces 712, 714 to match the interpupillary distance between the eyes of the user. In these instances, eye tracking devices may be included with a system described herein. In other embodiments, a combination of the foregoing are utilized to adjust the distance between the left and right eyepieces 712, 714 to match or substantially conform to the user's interpupillary distance.

A user 114 may adjust interpupillary distance based on the user's viewing of one or more fixation targets on one or more displays 215. For example, the displays 215 and the fixation targets may be configured such that the user views two aligned images, which may form a single, complete image when the interpupillary distance is appropriate for the user 114. The user 114 may adjust (for example, rotate) an adjustment control 204 to change the interpupillary distance based on the fixation target images, as shown in FIG. 7A. FIGS. 7B-7F illustrate one embodiment of fixation targets as seen by the viewer under a plurality of conditions; however, other fixation targets are possible, including but not limited to a box configuration. FIG. 7B shows a U-shaped fixation target 715a on the display 215a for the left eye. FIG. 7C shows an upside-down U-shaped fixation target 715b on the display 215b for the right eye.

When the interpupillary distance is appropriately adjusted, the bottom and top images 715a and 715b are aligned, as shown in FIG. 7D to form a complete H-shaped fixation target 715. When the interpupillary distance is too narrow, the fixation target 715a on the display 215a for the left eye appear shifted to the right and the fixation target on the display 215b for the right eye appear shifted to the left and the user sees the image shown in FIG. 7E. Conversely, when the interpupillary distance is too wide, the fixation target 715a on the display 215a for the left eye appear shifted to the left and the fixation target on the display 215b for the right eye appear shifted to the right and the user sees the image shown in FIG. 7F. Thus, the interpupillary distance may be adjusted based on these images.

In particular, in FIG. 7D, the alignment image 715 is in the shape of an "H." Thus, when the interpupillary distance is properly adjusted, the fixation targets on the left and right displays overlap to form an "H". Other alignment images 715 may be provided.

Figure 8:
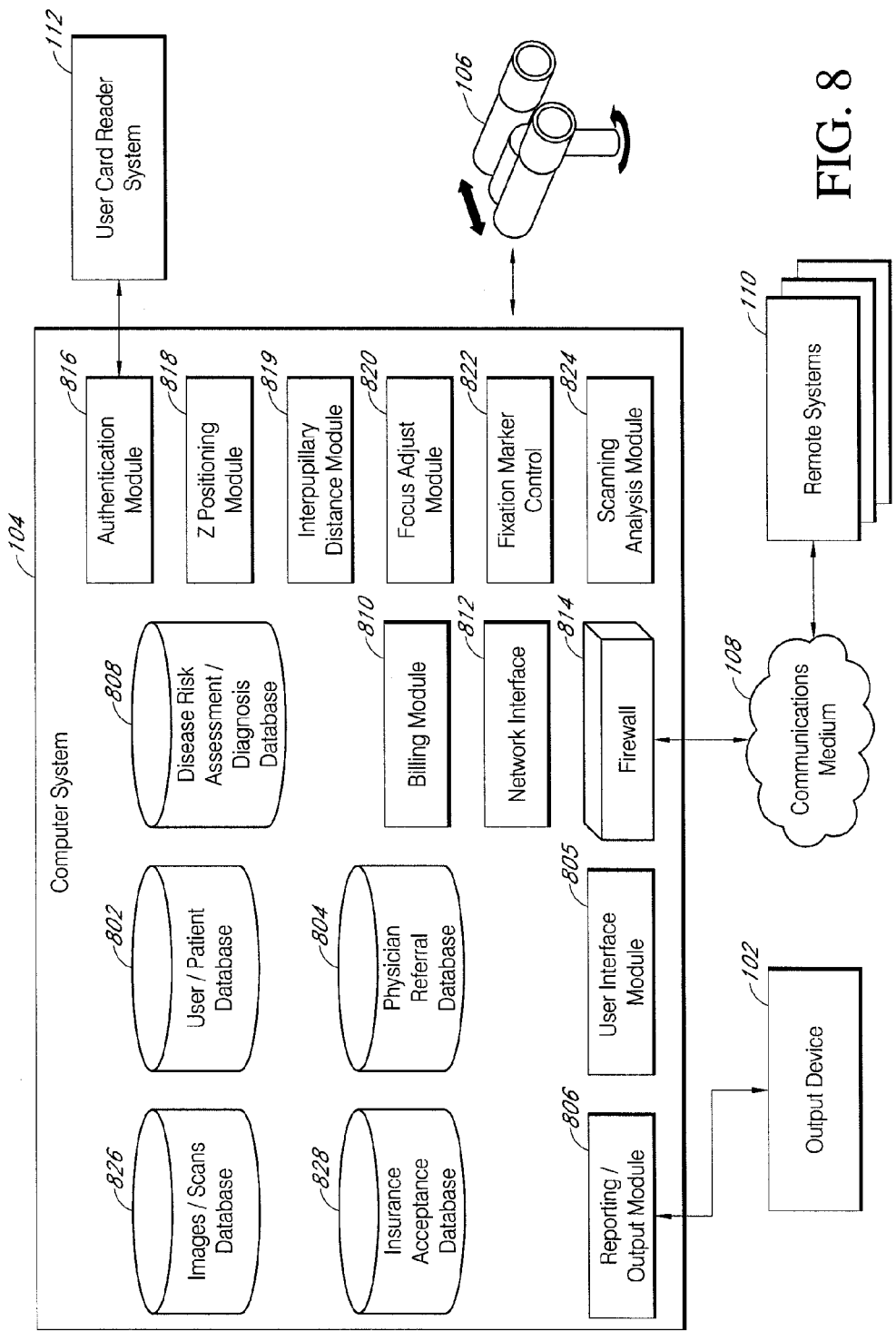
FIG. 8 is a block diagram schematically illustrating one embodiment of the computer system of the optical coherence tomography system described herein.

With reference to FIG. 8, there is illustrated an embodiment of the computer system 104. In the illustrated embodiment, the computer system 104 can comprise a scan control and analysis module 824 configured to control the scanning operations performed by the main body 106. The computer system 104 can also comprise a fixation marker control system 822 configured to display a fixation marker visible by the user from main body 106. In certain embodiments, the fixation marker is displayed as an "X," a dot, a box, or the like. The fixation marker can be configured to move horizontally, vertically, diagonally, circularly, or a combination thereof. The fixation marker can be repositioned quickly to relocate the beam location on the retina as the eye repositions itself. The computer system 104 can also comprise a focus adjust module 820 for automatically adjusting the focusing lenses in the main body 106 as further discussed herein. The computer system 104 can also comprise a Z positioning module 818 for automatically adjusting the Z offset as herein discussed.

Referring to FIG. 8, the computer system 104 comprises in the illustrative embodiment a disease risk assessment/diagnosis module 808 for storing and accessing information, data, and algorithms for determining, assessing the risk or likelihood of disease, and/or generating a diagnosis based on the data and/or measurements obtained from scanning the eyes of the user. In one embodiment, the scan control and analysis module 824 is configured to compare the data received from the main body 106 to the data stored in the disease risk assessment/diagnosis module 808 in order to generate a risk assessment and/or diagnosis of disease in the eyes of the user as further illustrated. The computer system 104 can also comprise an image/scans database configured to store images and/or scans generated by the main body 106 for a plurality of users, and to store a unique identifier associated with each image and/or scan. In certain embodiments, the scan control and analysis module 824 uses historical images and/or scans of a specific user to compare with current images and/or scans of the same user to detect changes in the eyes of the user. In certain embodiments, the scan control and analysis module 824 uses the detected changes to help generate a risk assessment and/or diagnosis of disease in the eyes of the user.

In the illustrative embodiment shown in FIG. 8, the computer system 104 can comprise a user/patient database 802 for storing and accessing patient information, for example, user name, date of birth, mailing address, residence address, office address, unique identifier, age, affiliated doctor, telephone number, email address, social security number, ethnicity, gender, dietary history and related information, lifestyle and/or exercise history information, use of corrective lens, family health history, medical and/or ophthalmic history, prior procedures, or other similar user information. The computer system 104 can also comprise a physician referral database for storing and accessing physician information, for example, physician name, physician training and/or expertise/specialty, physician office address, physician telephone number and/or email address, physician scheduling availability, physician rating or quality, physician office hours, or other physician information.

In reference to FIG. 8, the computer system 104 can also comprise a user interface module 805 (which can comprise without limitation commonly available input/output (I/O) devices and interfaces as described herein) configured to communicate, instruct, and/or interact with the user through audible verbal commands, a voice recognition interface, a key pad, toggles, a joystick handle, switches, buttons, a visual display, touch screen display, etc. or a combination thereof. In certain embodiments, the user interface module 805 is configured to instruct and/or guide the user in utilizing and/or positioning the main body 106 of the optical coherence tomography system 100. The computer system 104 can also comprise a reporting/output module 806 configured to generate, output, display, and/or print a report (for example, FIGS. 10A and 10B) comprising the risk assessment and/or diagnosis generated by the disease risk assessment/diagnosis module 808. In other embodiments, the report comprises at least one recommended physician to contact regarding the risk assessment.

Referring to FIG. 8, the computer system 104 can also comprise an authentication module 816 for interfacing with user card reader system 112, wherein a user can insert a user identification card into the user card reader system 112. In certain embodiments, the authentication module 816 is configured to authenticate the user by reading the data from the identification card and compare and/or store the information with the data stored in the user/patient database 802. In certain embodiments, the authentication module 816 is configured to read or obtain the user's insurance information from the user's identification card through the user card reader system 112. The authentication module 816 can be configured to compare the user's insurance information with the data stored in the insurance acceptance database 828 to determine whether the user's insurance is accepted or whether the user's insurance company will pay for scanning the user's eyes. In other embodiments, the authentication module communicates with the billing module 810 to send a message and/or invoice to the user's insurance company and/or device manufacturer to request payment for performing a scan of the patient's eyes. The card can activate one or more functions of the machine allowing the user, for example, to have a test performed or receive output from the machine. In other embodiments, the billing module 810 is configured to communicate with the user interface module 805 to request payment from the user to pay for all or some (for example, co-pay) of the cost for performing the scan. In certain embodiments, the billing module 810 is configured to communicate with the user card reader system 112 to obtain card information from the user's credit card, debit card, gift card, or draw down credit stored on the user's identification card. Alternatively, the billing module 810 is configured to receive payment from the user by communicating and/or controlling an interface device for receiving paper money, coins, tokens, or the like. Alternatively, the billing module 810 is configured to receive payment from the user by communicating with the user's mobile device through Bluetooth® or other communications protocols/channels in order to obtain credit card information, billing address, or to charge the user's mobile network service account (for example, the cellular carrier network).

With reference to FIG. 8, the user card may be used by insurers to track which users have used the system. In one embodiment, the system can print (on the face of the card) or store (in a chip or magnetic stripe) the scan results, risk assessment, and/or report directly onto or into the card that the patient inserts into the system (wherein the card is returned to the user). The system can be configured to store multiple scan results, risk assessments, and/or reports, and/or clear prior scan results, risk assessments, and/or reports before storing new information on the magnetic stripe. In certain embodiments, the calculation of the risk assessment is performed by the system (for example, scanning analysis module 824). In certain embodiments, the calculated risk assessment is transmitted a centralized server system (for example, remote systems 110) in another location that provides the results via a web page to physicians, users, patients, or the like. The centralized server system (for example, remote system 110) allows the user, patients, or doctors to enter their card code to see the results which are saved in the centralized database.

In the example embodiment of FIG. 8, the computer system 104 can comprise a network interface 812 and a firewall 814 for communicating with other remote systems 110 through a communications medium 108. Other remote systems 110 can comprise without limitation a system for checking the status/accuracy of the optical coherence tomography system 100; a system for updating the disease risk assessment/diagnosis database 808, the insurance acceptance database 828, the physician referral database 804, and/or the scan control and analysis module 824. In certain embodiments, the computer system 104 can be configured to communicate with a remote system 110 to conduct a primary and/or secondary risk assessment based on the data from scanning the user's eyes with the main body 106.

Referring to FIG. 8, the remote system 110 can be configured to remotely perform (on an immediate, delayed, and/or batch basis) a risk assessment and/or diagnosis and transmit through a network or communications medium the risk assessment, diagnosis, and/or report to the computer system 104 for output to the user using output device 102. In certain embodiments, the output device 102 is configured to display the risk assessment, diagnosis, and/or report as a webpage that can be printed, emailed, transmitted, and/or saved by the computer system 104. The remote system 110 can also be configured to transmit through a network or communications medium the risk assessment, diagnosis, and/or report to the user's (or doctor) cellular phone, computer, email account, fax, or the like.

Figure 9:
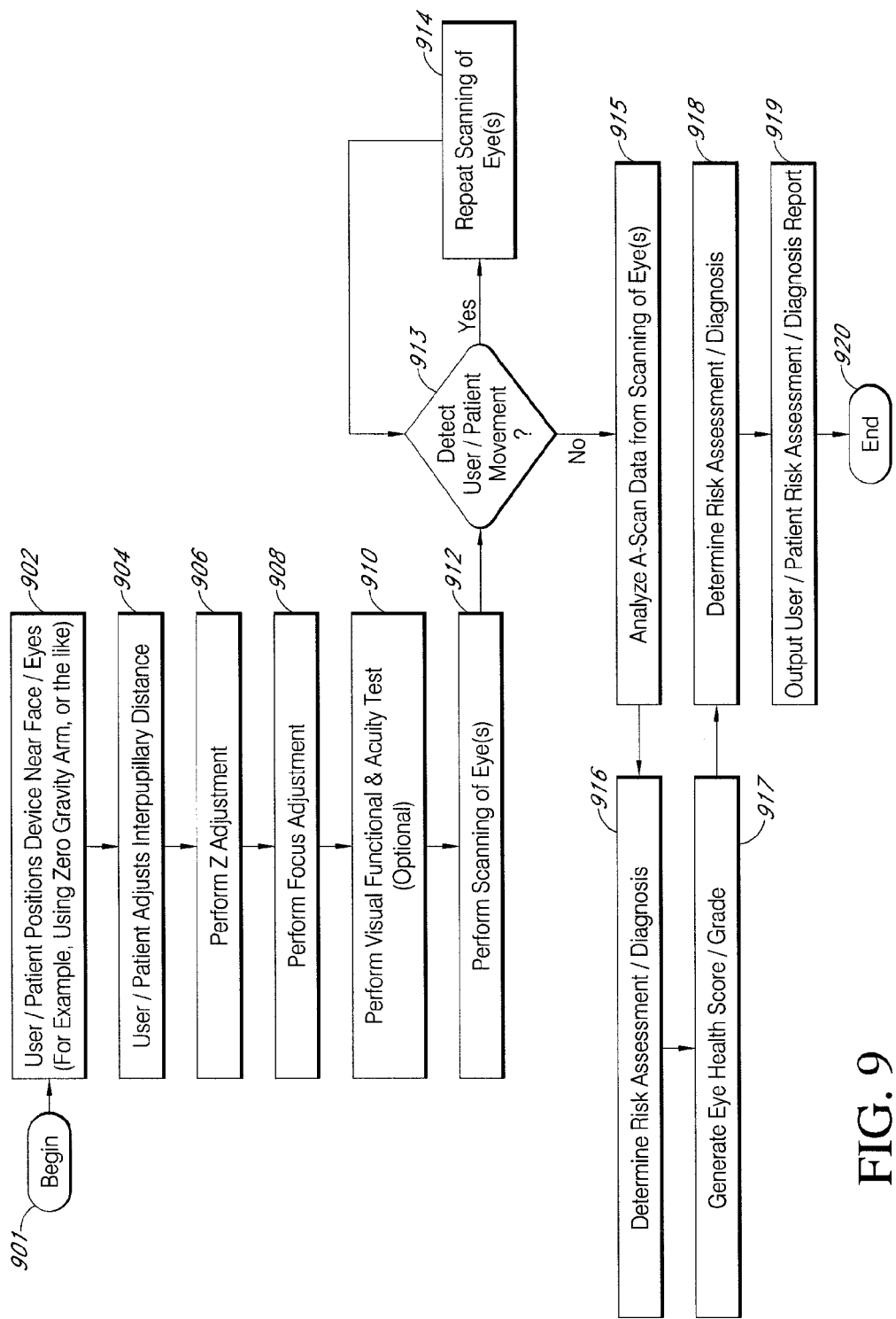
FIG. 9 is illustrates a process flow diagram of one embodiment of performing precision measurements on retinal tissue for the detection of pathognomonic disease features.

With reference to FIG. 9, there is shown an illustrated method of using the optical coherence tomography system 100 to self-administer an OCT scan of the user's eyes and obtain a risk assessment or diagnosis of various diseases and ailments. The process begins at block 901 wherein the user approaches the optical coherence tomography system 100 and activates the system, by for example pushing a button or typing in a activation code or anonymous identification number. In other embodiments, the user interface module 805 instructs users at block 901 to first insert an identification card or anonymous coded screening card in user card reader system 112 to activate the system. The system can also be activated at block 901 when users insert their user identification card in user card reader system 112. Other means of activating the system are possible as well as, including without limitation, a motion sensor, a weight sensor, a radio frequency identification (RFID) device, or other actuator to detect the presence of the user. Alternatively, the optical tomography system 100 can be activated when the billing module 810 detects that the user has inserted paper money, coins, tokens, or the like into an interface device configured to receive such payment. Alternatively, the billing module 810 can also be configured to activate the optical tomography system 100 when the billing module 810 communicates with a user's mobile device in order to obtain the user's credit card information, billing address, or the like, or to charge the user's mobile network service account (for example, the cellular carrier network)

In referring to FIG. 9 at block 902, the user interface module 805 is configured to direct the user to attach disposable eyecups onto the main body 106, and then position the main body 106 with the disposable eyecups near the eyes of the user and/or support the disposable eyecups against the user's eye socket. The user interface module 805 instructs the user to engage handle 118 to adjust the distance between the left and right eyepieces 612, 614 to match or substantially conform to the interpupillary distance of the user as described with respect to FIGS. 6A-6F. After the main body 106 and the interpupillary distance has been appropriately calibrated and/or adjusted by the user, the user inputs into or indicates to the user interface module 805 to begin the scan. The scan control and analysis module 824 substantially restricts movement or locks the position of the zero gravity arm and/or the distance between the left and right tubes 612, 614 to begin the scan.

Referring to FIG. 9, the Z module 818 automatically adjusts the z-offset in the main body 106 at block 906 such that the OCT measurement will be obtained, for example, from tissue in the retina. The Z module 818 may identify and/or estimate a position of part of the sample (for example, part of an eye of a user 114) and adjust the location of one or more optical components based on the position. One of ordinary skill in the art will appreciate the multitude of ways to perform such an adjustment. For example, the Z module 818 may comprise a motor, such as a piezoelectric motor, to translate the reference mirror/s longitudinally such that the optical path length from the beam splitter to the retina is about equal to (within a coherence length of) the optical path length in the reference arm. This movement may enable light from the reference arm to interfere with light reflected by a desired portion of the sample (for example, the retina). At block 908, the illustrative method performs a focus adjustment using the focus adjustment module 820. Those of ordinary skill in the art will also appreciate the different techniques for performing such auto-focus calibration. Block 910 illustrates an optional test performed by the computer system 104 to determine the visual functional and acuity of the user's eye. Such visual functional and acuity tests will be appreciated by those skilled in the art. In one embodiment, the visual acuity test works with or is combined with the fixation marker control system 722, and can test both eyes simultaneously or one eye at time. For example, the fixation marker will initially appear small and then gradually increase in size until the user indicates through the user interface module 705 that the fixation marker is visible. Based on the size at which the user can clearly see the fixation marker, fixation marker control system 722 can estimate or determine or assess the visual acuity of the user's eyes (for example, 20/20, 20/40, or the like).

With reference to FIG. 9 at Block 912, the user interface module 805 instructs the user to follow the movement of the fixation marker that is visible to the user from the main body 106. In one embodiment, the fixation marker control 822 is configured to display a fixation marker that moves horizontally. In some embodiments, the horizontal movement of the fixation marker allows the scan control and analysis module 824 to scan the eye vertically as the eye moves horizontally, thus possibly obtaining a two-dimensional, volume, or raster scan of the eye tissue at issue. Alternatively, the scan control and analysis module 824 and/or the fixation marker control may cause the fixation marker or the beam to jump or move around to obtain measurements at different lateral locations on the eye.

During the scanning of the eye, the scan control and analysis module 824 could be configured to detect at block 913 whether there has been a shift in the position of the main body 106 relative to the user. In one embodiment, the scan control and analysis module 824 can detect (in real-time, substantially real-time, or with a delay) whether a shift has occurred based on what the values the module 824 expects to receive during the scanning process. For example, as the scan control and analysis module 824 scans the retina, the module 824 expects to detect a change in signal as the scanning process approaches the optic nerve (for example, based on the location of the fixation target and/or state of the scanner(s)). Alternatively, the expected values or the expected change in values can also be determined or generated using a nomogram. If the system does not detect an expected signal change consistent with a detection of the optic nerve and/or receives no signal change, then the module 824 can be configured to interpret such data as the user is not tracking properly. Other features, for example, the fovea, or the like, can be used to determine whether the expected signal is observed. If improper tracking occurs enough (based on, for example, a threshold), the system 100 may request that the user fixate again (using fixation marker control 822) for another scan. If the foregoing shift detection process does not occur in real-time or substantially real-time, then the system can be configured to complete the scan, perform data analysis, and during the analysis the system can be configured to detect whether a shift occurred during the scan. If a substantial shift is detected, then the user may be instructed (through visual, audible, or verbal instructions using the user interface module 805) to sit forward again so another scan can be performed. If the system detects a shift 2 or 3 or more times, the system can be configured to refer the user to a general eye doctor.

At the end of a scan, the scan control and analysis module 824 can be configured to produce a confidence value that indicates how likely the nomograms will be to apply to this patient. For example, if the patient had borderline fixation, the confidence value might be lower than a patient whose fixation appeared to be good.

In the real-time embodiment, the system can be configured to perform rapid cross-correlations between adjacent A-scans or B-scans to make sure the eye is moving somewhat. In some embodiments, the foregoing can be advantageous for ANSI laser safety standards so as to avoid having users stare at the same location with laser energy bombarding the user's retina. Accordingly, in some embodiments, the system is configured with a laser time-out feature if the system detects no eye moment (for example, cross-correlations above a certain threshold). In some embodiments, to expedite this process and provide real time analysis in frequency domain OCT, signal data may be analyzed prior to performing an FFT. Other technologies can be used to determine that the user has some eye movement.

If no fixation problem has been detected, the scan control and analysis module 824 completes the scan of the user's eyes, stores the image and/or scan data in the images/scans database 826, and analyzes the A-scan data at block 915 to generate/determine a risk assessment and/or diagnosis at block 916 by accessing the data and/or algorithms stored in the disease risk assessment/diagnosis database 808. In some embodiments, groups of A-scans, partial or full B scans, or partial or full C-scan data can be analyzed.

As used herein the term "nomogram" generally refers to predictive tools, algorithms, and/or data sets. Nomograms in general can provide predictions for a user based on the comparison of characteristics of the user with the nomogram. The nomograms are derived, generated, calculated, or computed from a number, for example, hundreds, thousands, or millions of users/patients who exhibited the same condition (normal or diseased). In some embodiments described herein, nomograms compare the risk of having a disease based on physical characteristics. Accordingly, in some cases, nomograms can provide individualized predictions that are relative to risk groupings of patient populations who share similar disease characteristics. In some embodiments, nomograms can be used to provide the risk estimation or risk assessment on a 0-100% scale. Alternatively, nomograms used herein can provide an expected value, for example, at a certain position in the eye there is an expected eye thickness value of 100 microns.

Generally, nomograms have been developed and validated in large patient populations and are highly generalizable, and therefore, nomograms can provide the objective, evidence-based, individualized risk estimation or assessment. Accordingly, nomograms can be used as described herein to empower patients and allow them to better understand their disease. Further, nomograms as used herein can assist physicians with clinical decision-making and to provide consistent, standardized and reliable predictions.

Figure 10A:
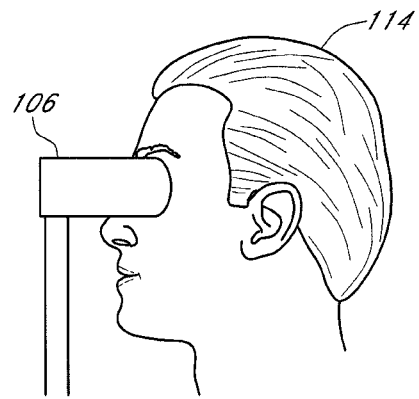
FIGS. 10A-10D illustrate possible embodiments of disposing the main body of an optical coherence tomography device with respect to a user.
Figure 10B:
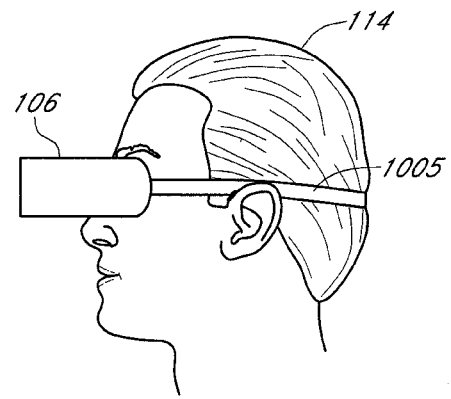

In the illustrative method shown in FIG. 9 at block 917, an eye health assessment or eye health grade report, as illustrated in FIGS. 10A and 10B, is generated for the user by accessing the disease risk assessment/diagnosis database 808. At block 918, the physician referral database 804 is accessed to generate a recommendation of when the user should visit a physician (for example, within one to two weeks). The physician referral database 804 is also accessed to generate, compile a listing of physicians suitable for treating the patient. The physician referral list can be randomly generated or selected based on referral fee payments paid by physicians, insurance companies, or based on location of the physician relative to the user's present location or office/home address, or based on the type of detected disease, or based on the severity of the detected disease, based on the location or proximity of the system relative the location of the physician, or based on a combination thereof. At block 919, the report is displayed to the user by using reporting/output module 806 and output device 102. In certain embodiments, the report data is stored in the user/patient database 802 for future analysis or comparative analysis with future scans.

In some embodiments, the main body 106 is not supported by the user 114. For example, the main body 106 may be supported by a free-standing structure, as shown in FIG. 10A. The user 114 may look into the eyepiece(s). The user 114 may be seated on a seating apparatus, which may include a height-adjusting mechanism. The main body 106 may supported by a height-adjustable support.

Figure 10C:
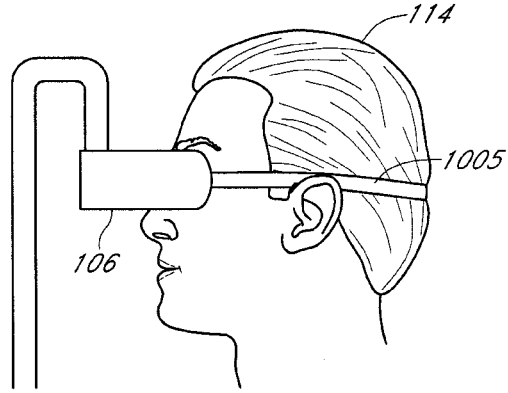

In some embodiments, such as those shown in FIGS. 10B-10C, a strap 1005 is connected to the main body 106. The strap may function to fully or partly support the main body 106, as shown in FIG. 10B. The strap 905 may be excluded in some embodiments. The main body 106 may be hand held by the user. In some embodiments, the main body 106 may be supported on eyewear frames. In some embodiments, all of the optics are contained within the main body 106 that is directly or indirectly supported by the user 114. For example, the main body 106 in FIG. 10B may include an optical coherence tomography system, an alignment system, and a data acquisition device. The data acquisition device may wirelessly transmit data to a network or computer system or may use a cable to transfer control signals. FIG. 10C is similar to that of FIG. 1 and is supported by a separate support structure (for example, an zero gravity arm). In some embodiments, a strap, belt, or other fastener assists in the alignment of the main body 106 with one or both eyes of the user 114.

Figure 10D:
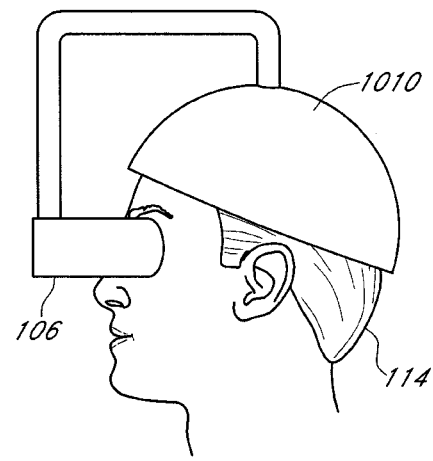

In some embodiments, as shown in FIG. 10D, the user wears an object 1010 connected to the eyepiece. The wearable object 1010 may include a head-mounted object, a hat or an object to be positioned on a user's head. As described above, in some embodiments, the main body 106 is supported on an eyewear frame worn by the user like glasses. The wearable object 1010 may fully or partly support the main body 106 and/or may assist in aligning the main body 106 with one or both eyes of the user 114.

Referring to FIGS. 11A and 11B, there are illustrated two example embodiments of the eye health grades and the eye health assessment reports. With reference to FIG. 11A, the eye health grades report can comprise without limitation a numeric and/or letter grade for each eye of the user for various eye health categories, including but not limited to macular health, optic nerve health, eye clarity, or the like. The eye health grades report can also comprise at least one recommendation to see or consult a physician within a certain period of time, and can provide at least one possible physician to contact. Data for generating the recommendation information and the list of referral physicians are stored in the physician referral database 804. In reference to FIG. 11B, the eye health assessment report can comprise a graphical representation for each eye of the user for various eye health categories. The report can be presented to the user on an electronic display, printed on paper, printed onto a card that the user inserted into the machine, electronically stored on the user's identification card, emailed to the user, or a combination thereof.

Figure 12:
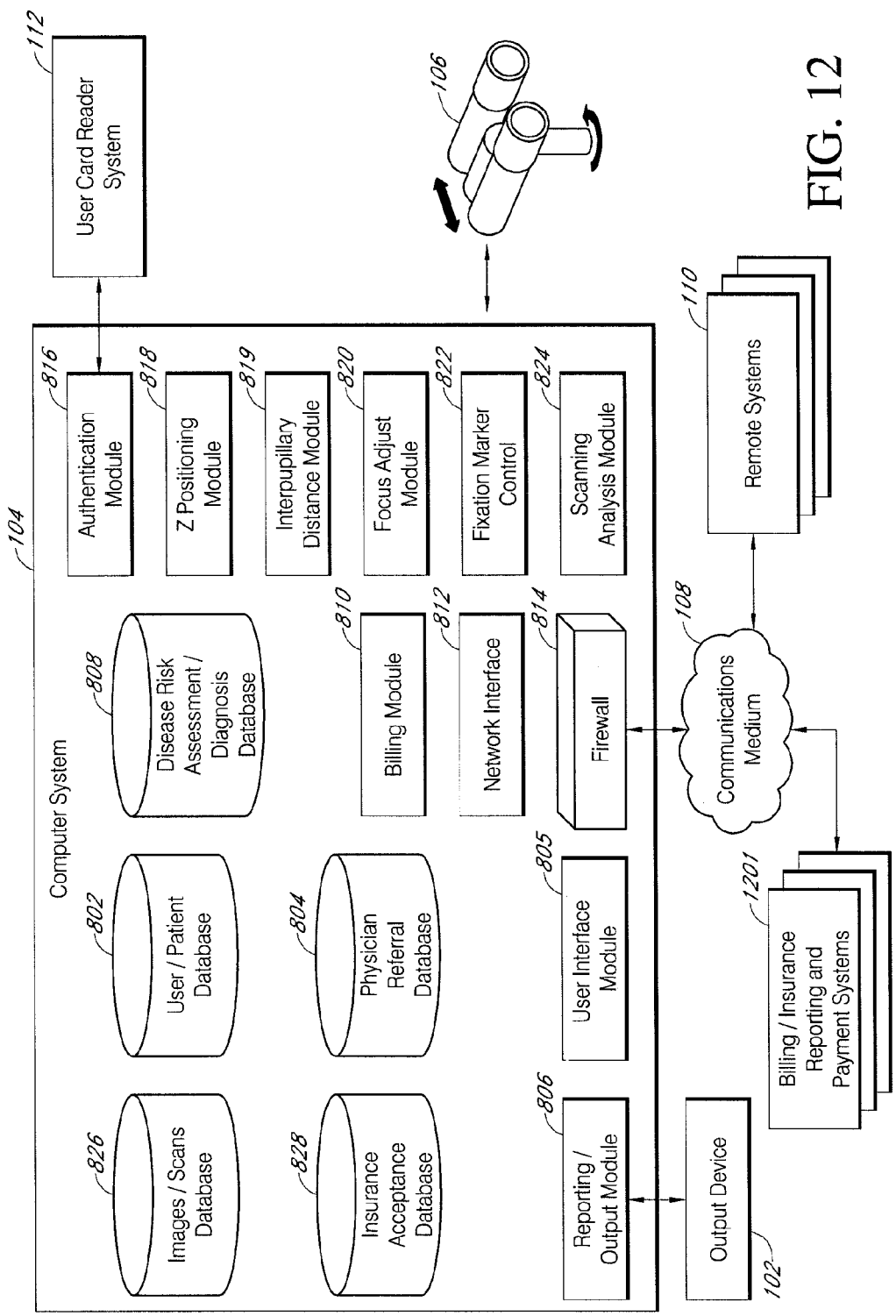
FIG. 12 is a block diagram schematically illustrating another embodiment of the computer system for a optical coherence tomography system described herein.

With reference to FIG. 12, there is illustrated another embodiment of the computer system 104 connected to remote system 110 and billing/insurance reporting and payment systems 1201. The billing module 810 can be configured to communicate with billing/insurance reporting payment systems 1201 through communications medium 108 in order to request or process an insurance claim for conducting a scan of the user's eyes. Based on communications with billing/insurance reporting and payment system 1201, the billing module 810 can also be configured to determine the amount payable or covered by the user's insurance company and/or calculate or determine the co-pay amount to be charge the consumer. In certain embodiments, the user can interact with the user interface module 805 to schedule an appointment with the one of the recommended physicians and/or schedule a reminder to be sent to the user to consult with a physician. The computer system 104 or a remote system 110 can be configured to send the user the reminder via email, text message, regular mail, automated telephone message, or the like.

Computing System

In some embodiments, the systems, computer clients and/or servers described above take the form of a computing system 1300 shown in FIG. 13, which is a block diagram of one embodiment of a computing system (which can be a fixed system or mobile device) that is in communication with one or more computing systems 1310 and/or one or more data sources 1315 via one or more networks 1310. The computing system 1300 may be used to implement one or more of the systems and methods described herein. In addition, in one embodiment, the computing system 1300 may be configured to process image files. While FIG. 13 illustrates one embodiment of a computing system 1300, it is recognized that the functionality provided for in the components and modules of computing system 1300 may be combined into fewer components and modules or further separated into additional components and modules.

Client/Server Module

In one embodiment, the system 1300 comprises an image processing and analysis module 1306 that carries out the functions, methods, and/or processes described herein. The image processing and analysis module 1306 may be executed on the computing system 1300 by a central processing unit 1304 discussed further below.

Computing System Components

In one embodiment, the processes, systems, and methods illustrated above may be embodied in part or in whole in software that is running on a computing device. The functionality provided for in the components and modules of the computing device may comprise one or more components and/or modules. For example, the computing device may comprise multiple central processing units (CPUs) and a mass storage device, such as may be implemented in an array of servers.

In general, the word "module," as used herein, refers to logic embodied in hardware or firmware, or to a collection of software instructions, possibly having entry and exit points, written in a programming language, such as, for example, Java, C or C++, or the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the computing system 1300 also comprises a mainframe computer suitable for controlling and/or communicating with large databases, performing high volume transaction processing, and generating reports from large databases. The computing system 1300 also comprises a central processing unit ("CPU") 1304, which may comprise a conventional microprocessor. The computing system 1300 further comprises a memory 1305, such as random access memory ("RAM") for temporary storage of information and/or a read only memory ("ROM") for permanent storage of information, and a mass storage device 1301, such as a hard drive, diskette, or optical media storage device. Typically, the modules of the computing system 1300 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The example computing system 1300 comprises one or more commonly available input/output (I/O) devices and interfaces 1303, such as a keyboard, mouse, touchpad, and printer. In one embodiment, the I/O devices and interfaces 1303 comprise one or more display devices, such as a monitor, that allows the visual presentation of data to a user. More particularly, a display device provides for the presentation of GUIs, application software data, and multimedia presentations, for example. In the embodiment of FIG. 13, the I/O devices and interfaces 1303 also provide a communications interface to various external devices. The computing system 1300 may also comprise one or more multimedia devices 1302, such as speakers, video cards, graphics accelerators, and microphones, for example.

Computing System Device/Operating System

The computing system 1300 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 1300 is generally controlled and coordinated by operating system software, such as z/OS, Windows 95, Windows 98, Windows NT, Windows 2000, Windows XP, Windows Vista, Linux, BSD, SunOS, Solaris, or other compatible operating systems. In Macintosh systems, the operating system may be any available operating system, such as MAC OS X. In other embodiments, the computing system 1300 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 13, the computing system 1300 is coupled to a network 1310, such as a modem system using POTS/PSTN (plain old telephone service/public switched telephone network), ISDN, FDDI, LAN, WAN, or the Internet, for example, via a wired, wireless, or combination of wired and wireless, communication link 1315. The network 1310 communicates (for example, constantly, intermittently, periodically) with various computing devices and/or other electronic devices via wired or wireless communication links. In the example embodiment of FIG. 13, the network 1310 is communicating with one or more computing systems 1317 and/or one or more data sources 1319.

Access to the image processing and analysis module 1306 of the computer system 1300 by remote computing systems 1317 and/or by data sources 1319 may be through a web-enabled user access point such as the computing systems' 1317 or data source's 1319 personal computer, cellular phone, laptop, or other device capable of connecting to the network 1310. Such a device may have a browser module implemented as a module that uses text, graphics, audio, video, and other media to present data and to allow interaction with data via the network 1310.

The browser module or other output module may be implemented as a combination of an all points addressable display such as a cathode-ray tube (CRT), a liquid crystal display (LCD), a plasma display, or other types and/or combinations of displays. In addition, the browser module or other output module may be implemented to communicate with input devices 1303 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module or other output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1300 may comprise a physical or logical connection established between a remote microprocessor and a mainframe host computer for the express purpose of uploading, downloading, or viewing interactive data and databases on-line in real time. The remote microprocessor may be operated by an entity operating the computer system 1300, including the client server systems or the main server system, and/or may be operated by one or more of the data sources 1319 and/or one or more of the computing systems. In some embodiments, terminal emulation software may be used on the microprocessor for participating in the micro-mainframe link.

In some embodiments, computing systems 1317 that are internal to an entity operating the computer system 1300 may access the image processing and analysis module 1306 internally as an application or process run by the CPU 1304.

User Access Point

In one embodiment, a user access point comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 13, the network 1310 may communicate with other data sources or other computing devices. The computing system 1300 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Figure 14A:
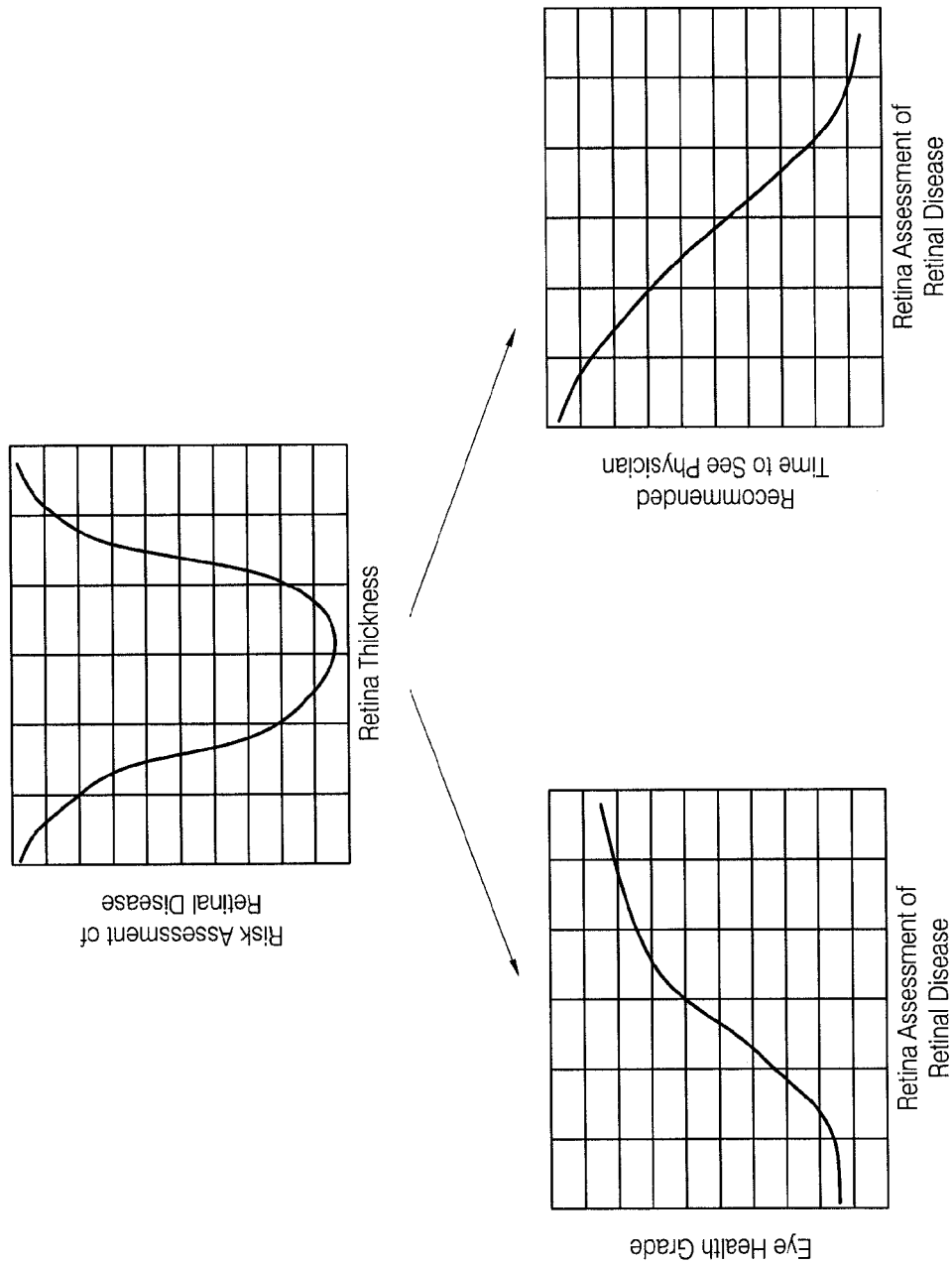
FIG. 14A is a diagram schematically illustrating one embodiment for determining a risk assessment.

With reference to FIG. 14A, there is illustrated an example method for determining or generating a risk assessment of a disease, such as an eye disease, thereby allowing the generation of a health grade and recommended time to see a physician. The example shown in FIG. 14A is for retinal disease, however, the process and method illustrated can be used for other diseases or eye diseases. In this example, the scan control and analysis module 824 is configured to determine the thickness of the retina based on the A-scan data derived from the main body 106. This data may include but is not limited to A-scan data from different A-scans. The scan control and analysis module 824 can also be configured to access data and algorithms in the disease risk assessment/diagnosis database 808 to calculate the risk assessment of retinal disease based on the measured thickness of the retina as illustrated by the function curve in FIG. 14A. The reporting/output module 806 can be configured to normalize the calculated risk assessment value into an eye health letter or numerical grade or score. The reporting/output module 806 can also be configured to access data and algorithms in the physician referral database 804 to calculate a recommended time to see a physician based on the calculated risk assessment value.

Figure 14B:
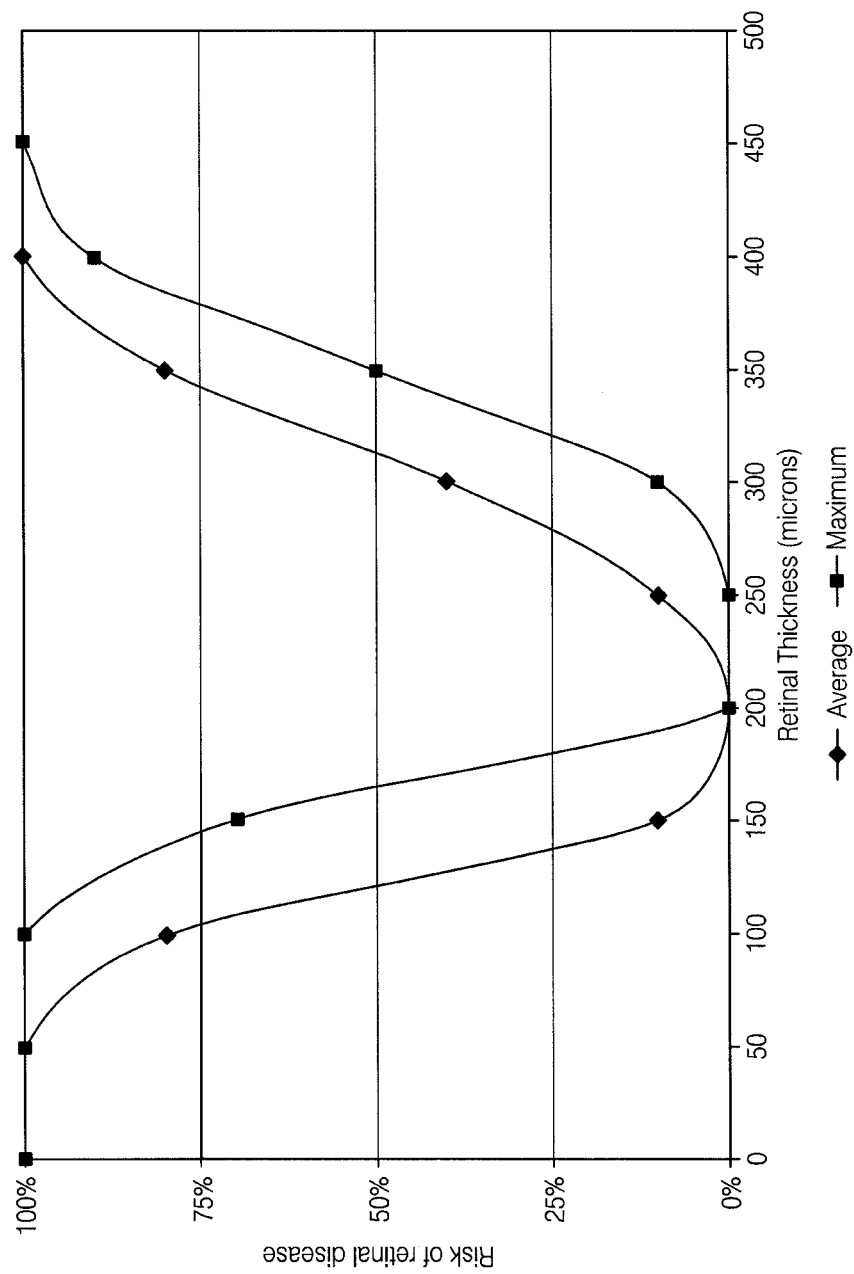
FIG. 14B is a schematic illustration of a plot of risk of retinal disease versus retinal thickness for determining a risk assessment in another embodiment.

With reference to FIG. 14B, there is illustrated another example method or process for determining or generating a risk assessment of disease by comparing the scan data to the disease risk assessment/diagnosis database 808 comprising, for example, minimum and maximum thickness data and algorithms, and such minimum and maximum thickness data and algorithms that can be based on or are in the form of nomograms. In certain embodiments, the system is configured to generate scan data for portions of the eye scanned to determine thickness of the retina at any one point, and compare such data to histograms and/or nomograms (for example, nomograms that show expected thickness at said location likelihood of or disease for a given thickness) to derive a risk assessment. The system can also be configured to generate an average thickness for the entire retina that is scanned, and compare such data to histograms and/or nomograms to derive a risk assessment.

The term "histogram" as used herein generally refers to an algorithm, curve, or data or other representation of a frequency distribution for a particular variable, for example, retinal thickness. In some cases, the variable is divided into ranges, interval classes, and/or points on a graph (along the X-axis) for which the frequency of occurrence is represented by a rectangular column or location of points; the height of the column and/or point along the Y-axis is proportional to or otherwise indicative of the frequency of observations within the range or interval. "Histograms," as referred to herein, can comprise measured data obtained, for example, from scanning the eyes of a user, or can comprise data obtained from a population of people. Histograms of the former case can be analyzed to determine the mean, minimum, or maximum values, and analyze changes in slope or detect shapes or curvatures of the histogram curve. Histograms of the latter case can be used to determine the frequency of observation of a measured value in a surveyed sample.

In the instance where an average thickness value is derived from the scan data, there are some conditions/diseases that may be indicated by thickening of the retina in a localized area. Accordingly, such a condition may not significantly affect the average thickness value (for example, if a substantial portion of the retina is of normal thickness). Therefore, the maximum thickness value may be needed to detect this abnormal thickening in the retina. In some embodiments, this maximum thickness value may be due to a segmentation error. Accordingly, a more stable way of determining the maximum value may also be to use the value corresponding to 95% (or any value between 75% and 99%) maximal thickness. The foregoing can also be applied to minimum retinal thickness or any other value, measurement, and/or detectable condition in the eye. For example, with minimum retinal thickness, if the user has a macular hole, there will only be a small area of zero thickness, and possibly not enough to significantly reduce the average thickness, but definitely an abnormality that may be detected.

In other embodiments, the system may be configured to create histograms of measured thickness and/or measured intensity values and/or slopes or derivatives of intensity values and/or variables to identify abnormalities. For example, changes or substantial changes in slope (calculated as the derivative of adjacent intensity values) may indicate hyporeflective or hyperreflective structures that may not affect mean or average intensity values, but may be indicative of disease or conditions. For example, the system can determine if the distribution of retinal thicknesses across the measured portion of the retina matches that of the normal population. Deviation from such a "normal" histogram would result in lower health grades/higher risk assessments.

In various embodiments, the methods or processes described herein can be used to determine or generate a risk assessment of maculopathy based, for example, on abnormal thickening of the retina or fovea, the presence of hyperreflective (bright or high intensity) or hyporeflective (dark or low intensity) structures in the outer half of the retina, the presence of hyporeflective (dark) structures in the inner half of the retina, the presence of irregularities in the contour of the retinal pigment epithelium that depart from the normal curvature of the eye, or of the presence of hypertransmission of light through the retinal pigment epithelium when compared to a database of normal values stored in the disease risk assessment/diagnosis database 708.

As described above, there are several ways to detect or generate a risk assessment for several diseases or conditions. In certain embodiments, scan data is compared to data found in normal people to identify similarities or differences from a nomogram and/or histogram. In other embodiments, scan data is compared to data found in people with diseases to identify similarities or differences from nomograms and/or histograms. The pathognomonic disease features could be indicated by similarity to nomograms, for example, images, histograms, or other data, etc. from diseased patients.

In one embodiment, "normal" data (for example, histograms) are created for retinal thickness in each region of the retina (optic nerve, fovea, temporal retina) and compare to measured, detected, scanned, or encountered values to these "normal" data (for example, histograms) to determine relative risks of retinal disease or other diseases. The same can be performed for nerve fiber layer (NFL) thickness to detect glaucoma. In other embodiments, the detection or generation of a risk assessment for glaucoma is performed or generated by analyzing collinear A-scan data to see if curvilinear thinning indicates the presence of glaucoma because glaucoma tends to thin the NFL in curvilinear bundles. The NFL radiates out from the optic nerve in a curvilinear fashion like iron filings around a magnet. Measuring and analyzing a sequence of A-scan data that follow such a curvilinear path may be useful to identify such thinning that is characteristic of glaucoma. The analysis could be centered on and/or around the optic nerve or centered on and/or around the fovea or elsewhere. In another embodiment, the detection and/or generation of a risk assessment for glaucoma is performed or generated by analyzing the inner surface of the optic nerve to determine the optic disc cup volume.

The system can also be configured to detect and/or generate a risk assessment for optical clarity wherein the system integrates A-scan data in the Z direction and compares some or all the A-scan data to a nomogram value or values, or, for example, a histogram. In general, darker A-scans will probably indicate the presence of media opacities, for example, cataracts, that decrease optical clarity (therefore, increase the subject's risk of having an optical clarity problem, for example, cataracts).

Figure 15:
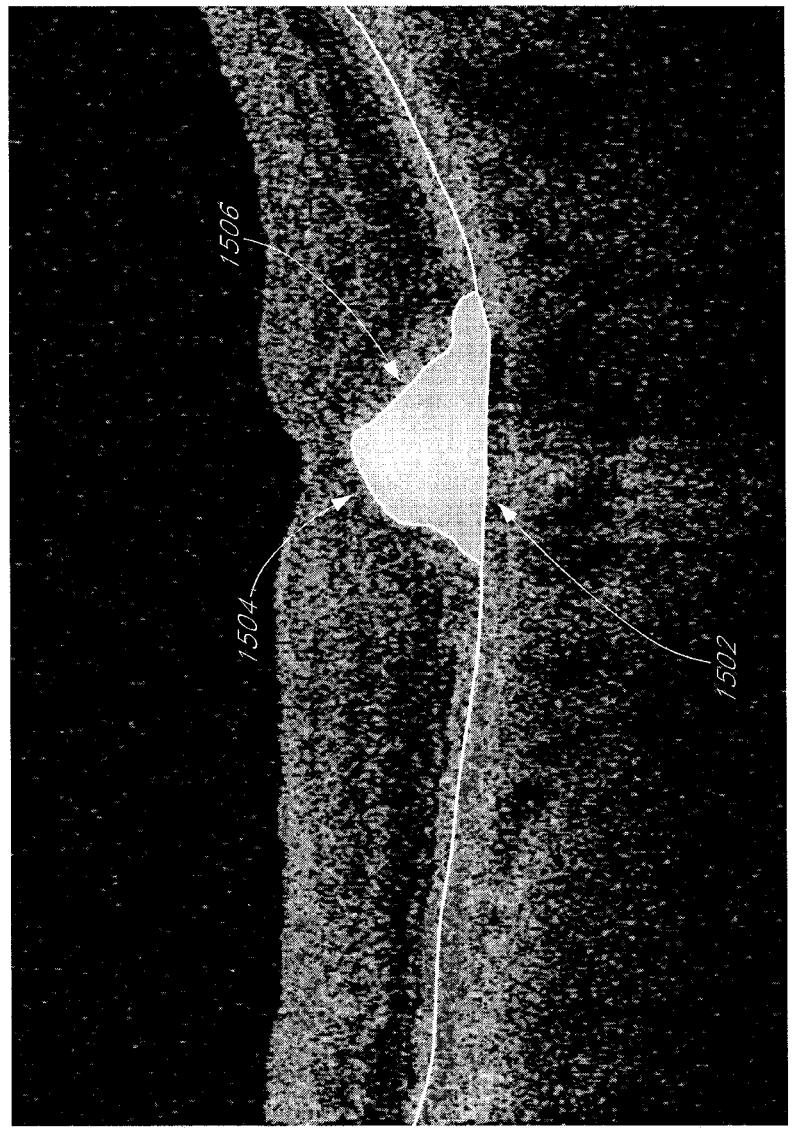

The system can also be configured to detect or generate risk assessments for retinal pigment epithelium (RPE) features that depart from the normal curvature of the eye (drusen, retinal pigment epithelial detachments). Such RPE features can be detected by fitting the detected RPE layer to a polynomial curve that mimics the expected curvature for the eye, and using a computer algorithm to analyze, compare, or examine the difference between these curves. For example with respect to FIG. 15, the system can be configured to subtract the polynomial curve that mimics the expected curvature of the RPE layer 1502 from the detected RPE layer curve 1504, and analyze and/or compare the resulting difference/value 1506 with the values (for example, in a histogram or nomogram) from normal and/or diseased eyes to generate a diagnosis or risk assessment. The foregoing method and process is similar to a measure of tortuosity in that a bumpy RPE detection will generally have more deviations from a polynomial curve than smooth RPE detections, which are common in young, healthy people.

Such RPE detection can also be used to detect increased transmission through the RPE which is essentially synonymous with RPE degeneration or atrophy. In certain embodiments, the system is configured to analyze the tissue layer beyond or beneath the RPE layer. Using imaging segmentation techniques, the RPE layer can be segmented. In certain embodiments, the system is configured to add up all of the intensity values beneath the RPE detection. When atrophy is present, there are generally many high values beneath the RPE line, which makes the integral value high and would increase the patient's risk of having a serious macular condition, such as geographic atrophy.

Figure 16:
FIG. 16 is an illustration of retinal tissue segmented into inner and outer retinal tissue regions.

With reference to FIG. 16, the system can also be used to detect or generate risk factors for abnormal intensities within the retina. In certain embodiments, the system is configured to divide the retina into an inner 1602 and outer 1604 half based on the midpoint between the internal limiting membrane (ILM) detection 1606 and the RPE detection lines 1608. In some instances, a blur filter (for example, a Gaussian blur, radial blur, or the like) is applied to the retinal tissue to remove speckle noise and/or other noise. For each the inner and outer retina regions, a first derivative of the intensity values (with respect to position, for example, d/dx, d/dy, or the like) can be calculated to determine the slope of the curve to differentiate the areas where there are large changes from dark to bright or vice versa across lateral dimensions of the tissue. For example, intensities or derivatives within the retina can be compared to, for example, normal histograms, wherein inner retinal hypointensity can be an indicator of cystoid macular edema; or wherein outer retinal hypointensity can be an indicator of cystoid macular edema, subretinal fluid, or diffuse macular edema; or wherein outer retinal hyperintensity can be an indication of diabetes (which may be the cause of diabetic retinopathy, or damage to the retina due to, for example, complications of diabetes mellitus), or age-related macular degeneration.

Data from normal patients can used to compile histograms of intensity and/or slope (derivative) data to indicate expected values for normal people. Data from people with various diseases can also be placed into histograms of intensity and/or derivative (slope) values to indicate expected values for those people with diseases. In certain embodiments, a relative risk will then be developed for each entry on the histogram such that this risk can be applied to unknown cases. For example, in some instances, people with 10% of their outer retinal intensity values equal to 0 have an 85% chance of having a retinal problem. Accordingly, such users may receive a health grade of 15. In another example, people with any inner retinal points less than 10 have a 100% chance of disease, and therefore such users may receive a health grade of 5.

Alternatively, as discussed herein, the foregoing method or process can also be used to determine or generate a risk assessment of glaucoma based on patterns of thinning of the macular and/or peripapillary nerve fiber layer or enlarged cupping of the optic nerve head as compared to a database of normal and abnormal values stored in the disease risk assessment/diagnosis database 708. Similarly, to detect or develop a risk assessment for uveitis, a histogram of expected intensity values above the inner retinal surface (in the vitreous), for example, can be used. The presence of large, bright specks (for example, high intensity areas) in the vitreous cavity would indicate possible uveitis and would likely indicate a need for referral. The foregoing method and process can also be used to determine or generate a risk of eye disease based on the intensity levels of the image signal as compared to a database of normal and abnormal values stored in the disease risk assessment/diagnosis database 708.

In other embodiments, the foregoing method and process can also be used to determine or generate a risk assessment of uveitis based on hyperreflective features in the vitreous cavity as compared to normal and abnormal hyperreflective features stored in the disease risk assessment/diagnosis database 708. The foregoing method and process can also be used to determine or generate a risk assessment of anterior eye disease based on detection of pathognomonic disease features, such as cystoid retinal degeneration, outer retinal edema, subretinal fluid, subretinal tissue, macular holes, drusen, retinal pigment epithelial detachments, and/or retinal pigment epithelial atrophy, wherein the detected features are compared with such pathognomonic disease features stored in the disease risk assessment/diagnosis database 708. In certain embodiments, the system is configured to perform template matching wherein the system detects, compares, and/or matches characteristics from A-scans generated from scanning a user, also known as unknown A-scans, with a database of patterns known to be associated with disease features, such as subretinal fluid, or the like.

With reference to FIGS. 1, 8 and 9, the optical coherence tomography system 100 is configured to allow the user to self-administer an OCT scan of the user's eyes without dilation of the eyes, and obtain a risk assessment or diagnosis of various diseases and ailments without the engaging or involving a doctor and/or technician to align the user's eyes with the system, administer the OCT scan and/or interpret the data from the scan to generate or determine a risk assessment or diagnosis. In one embodiment, the optical coherence tomography system 100 can perform a screening in less than two minutes, between 2-3 minutes, or 2-5 minutes. In certain embodiments, the use of the binocular system allows the user to self-align the optical coherence tomography system 100.

The optical coherence system 100 with a binocular system is faster since it scans both eyes without repositioning and can allow the optical coherence tomography system 100 to scan a person's bad eye because the person's bad eye will follow the person's good eye as the latter tracks the fixation marker. Accordingly, the optical coherence tomography system 100 reduces the expense of conducting an OCT scan, thereby making OCT scanning more accessible to more people and/or users, and saving millions of people from losing their eye sight due to eye diseases or ailments that are preventable through earlier detection. In one embodiment, the optical coherence tomography system 100 is configured to have a small-foot print and/or to be portable, such that the optical coherence tomography system 100 can be installed or placed in drug stores, retail malls or stores, medical imaging facilities, grocery stores, libraries, and/or mobile vehicles, buses, or vans, a general practitioner's or other doctor's office, such that the optical coherence tomography system 100 can be used by people who do not have access to a doctor.

All of the methods and processes described above may be embodied in, and fully automated via, software code modules executed by one or more general purpose computers or processors. The code modules may be stored in any type of computer-readable medium or other computer storage device. Some or all of the methods may alternatively be embodied in specialized computer hardware.

While the invention has been discussed in terms of certain embodiments, it should be appreciated that the invention is not so limited. The embodiments are explained herein by way of example, and there are numerous modifications, variations and other embodiments that may be employed that would still be within the scope of the present invention.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. A method for administering an optical coherence tomography scan, the method comprising:
    positioning an optical coherence tomography instrument onto at least one user eye, wherein the positioning is performed by the user; and
    activating the optical coherence tomography instrument by the user to begin the optical coherence tomography scan, wherein the optical coherence tomography instrument is configured to scan the at least one user eye, and wherein the optical coherence tomography instrument comprises:
    at least one ocular for directing light to and receiving light from the at least one user eye;
    a light source that outputs light that is directed through the at least one user eye;
    an interferometer configured to produce optical interference using light reflected from the subject's eye;
    an optical detector disposed so as to detect the optical interference; and
    an auto-focus lens configured to focus the instrument based on the detected optical interference.

2. The method of claim 1, wherein the optical coherence tomography instrument is activated via a button, keypad, toggle, touch pad, touch sensor, foot pedal, knob, rotating handle, or microphone.

3. The method of claim 1, wherein activating the instrument comprises entering an input by the user.

4. The method of claim 1, wherein activating the instrument comprises using a card and a card reader, wherein the card reader is configured to read the card.

5. The method of claim 4, wherein the card comprises user identification data.

6. The method of claim 1, wherein activating the instrument comprises triggering an actuator by the user, wherein the actuator is configured to detect the presence of the user near the optical coherence tomography instrument.

7. The method of claim 6, wherein the actuator is a motion sensor, a weight sensor, and/or a radio frequency identification device.

8. The method of claim 1, wherein activating the instrument comprises rendering payment by the user to an interface device.

9. The method of claim 1, wherein activating the instrument comprises interfacing by the user a mobile phone of the user's with a billing module, such that the billing module obtains user data.

10. The method of claim 9, wherein the user data is credit card information and/or a billing address.

11. An optical coherence tomography system for providing a self-administered scan, the system comprising:
    an eyepiece for receiving at least one eye of a user;
    a light source that outputs light that is directed through the eyepiece into the at least one eye of the user;
    an interferometer configured to produce optical interference using light reflected from the at least one eye of the user;
    an optical detector disposed so as to detect the optical interference;
    electronics coupled to the detector and configured to provide an output based on optical coherence tomography measurements obtained using the interferometer; and
    an auto-focus lens configured to focus the instrument based on the detected optical interference,
    wherein the scan is configured to be activated by the user.

12. The optical coherence tomography system of claim 11, wherein the scan is configured to be activated by the user via a button, keypad, toggle, touch pad, touch sensor, foot pedal, knob, rotating handle, or microphone.

13. The optical coherence tomography system of claim 11, further comprising:
    a user interface module configured to:
        receive an input entered by the user; and
        activate the scan based at least in part on the input entered by the user,
        wherein the input comprises an activation code or an identification number.

14. The optical coherence tomography system of claim 11, further comprising:
    a card reader configured to:
        read user identification data from a card; and
        activate the scan based at least in part on the user identification data read from the card.

15. The optical coherence tomography system of claim 14, wherein the user identification data comprises the name, the birth date, and/or the billing address of the user.

16. The optical coherence tomography system of claim 11, further comprising:
    an actuator configured to detect a presence of the user near the optical coherence tomography system, said scan being activated based at least in part on an indication of the presence of the user near the optical coherence tomography system.

17. The optical coherence tomography system of claim 16, wherein the actuator is a motion sensor, a weight sensor, or a radio frequency identification device.

18. The optical coherence tomography system of claim 11, further comprising:
    a billing module configured to:
        receive payment rendered by the user; and
        activate the scan based at least in part on the payment rendered by the user.

19. The optical coherence tomography system of claim 11, further comprising:
    a billing module configured to:
        interface with a mobile phone of the user's; and
        obtain user data based at least in part on the interface with the mobile phone of the user's.

20. The optical coherence tomography system of claim 19, wherein the user data is credit card information and/or a billing address.

21. The method of claim 1, wherein activating the instrument comprises interfacing by the user a mobile device of the user's with an interface module.

22. The method of claim 21, wherein the mobile device is a mobile phone.

23. The optical coherence tomography system of claim 11, further comprising an interface module configured to interface with a mobile device of the user's.

24. The optical coherence tomography system of claim 23, wherein the mobile device is a mobile phone.

\* \* \* \* \*